(12) United States Patent
Sampson et al.

(10) Patent No.: US 7,399,844 B2
(45) Date of Patent: *Jul. 15, 2008

(54) METHOD AND REAGENTS FOR ANALYZING THE NUCLEOTIDE SEQUENCE OF NUCLEIC ACIDS

(75) Inventors: Jeffrey R. Sampson, Burlingame, CA (US); Joel Myerson, Berkeley, CA (US); Anna M. Tsalenko, Chicago, IL (US); Nicholas M. Sampas, San Jose, CA (US); Peter G. Webb, Menlo Park, CA (US); Zohar H. Yakhini, Ya'Acov (IL)

(73) Assignee: Agilent Technologies, Inc., Santa Clara, CA (US)

( * ) Notice: Subject to any disclaimer, the term of this patent is extended or adjusted under 35 U.S.C. 154(b) by 1260 days.

This patent is subject to a terminal disclaimer.

(21) Appl. No.: 09/836,012

(22) Filed: Apr. 17, 2001

(65) Prior Publication Data

US 2002/0182601 A1    Dec. 5, 2002

Related U.S. Application Data

(63) Continuation-in-part of application No. 09/112,437, filed on Jul. 9, 1998, now Pat. No. 6,218,118.

(51) Int. Cl.
    *C07H 19/00*     (2006.01)
    *C12Q 1/68*     (2006.01)

(52) U.S. Cl. .................................. 536/22.1; 435/6

(58) Field of Classification Search ............... 435/6, 435/7.1, 91.1, 91.2, 267.1; 536/22.1, 23.1, 536/24.3–24.33
See application file for complete search history.

(56) References Cited

U.S. PATENT DOCUMENTS

| 5,654,413 | A * | 8/1997 | Brenner ..................... 536/22.1 |
| 6,218,118 | B1 * | 4/2001 | Sampson et al. ............... 635/6 |
| 6,607,878 | B2 * | 8/2003 | Sorge ............................ 435/6 |

FOREIGN PATENT DOCUMENTS

| EP | 0778280 A2 | 1/1994 |
| EP | 0778280 A | 6/1997 |
| WO | WO 9504160 A1 * | 2/1995 |
| WO | WO98/10095 | 9/1997 |
| WO | WO98/31830 | 1/1998 |
| WO | WO98/31836 | 1/1998 |
| WO | WO 98/10095 A | 3/1998 |
| WO | WO 98/31830 A | 7/1998 |
| WO | WO 98/31836 A | 7/1998 |
| WO | WO99/32501 | 7/1999 |
| WO | WO 99/32501 A | 7/1999 |
| WO | WO00/03038 | 1/2000 |
| WO | WO 00/03038 A | 1/2000 |

OTHER PUBLICATIONS

Radoje Drmanac, Ivan Labat, Ivan Brukener, and Radomir Crkvenjakov; "Sequencing of Megabase Plus DNA by Hybridization: Theory of the Method"; Genomics, vol. 4; pp. 114-128.
Andrei D. Mirzabekov; "DNA sequencing by hybridization—a megasequencing method and a diagnostic tool?"; Tibtech, Jan. 1194, vol. 12;pp. 27-32.
Drmanac, R., et al., "Sequencing of Megabase Plus DNA Hybridization: Theory of the Method", Genomcis Academic Pres, San Diego, U. S., vol. 4, 1989, pp. 114-128.
Mirzabekov, A. D., "DNA Sequencing by Hybridization—A Megasequencing Method and a Diagnostic Tool?"; Trends in Biotechnology, Elsevier, Amsterdam. GB, vol. 12, No. 1, 1994, pp. 27-32.

* cited by examiner

*Primary Examiner*—Suryaprabha Chunduru

(57) ABSTRACT

Methods and reagents are disclosed which provide for more sensitive, more accurate and higher through-put analyses of target nucleic acid sequences. The methods and reagents of the present invention may be generically applied to generally any target nucleic acid sequence and do not require a priori information about the presence, location or identity of mutations in the target nucleic acid sequence. The reagents of the invention are mixtures of oligonucleotide precursors having a high level of coverage and mass number complexity, and also having tags analyzable by mass spectrometry which are covalently linked to the precursors through cleavable bonds. A method is also disclosed for analyzing a target nucleic acid sequence employing the mixtures of oligonucleotide precursors having tags analyzable by mass spectrometry covalently linked to the oligonucleotide precursors through cleavable bonds, and chemical or enzymatic assays to alter the mass of the oligonucleotide precursors prior to mass spectral analysis. The enzymatic assay may be a polymerase extension assay or a ligation-based assay. The kits for carrying out the methods of the invention are also disclosed.

6 Claims, 13 Drawing Sheets

Figure 1
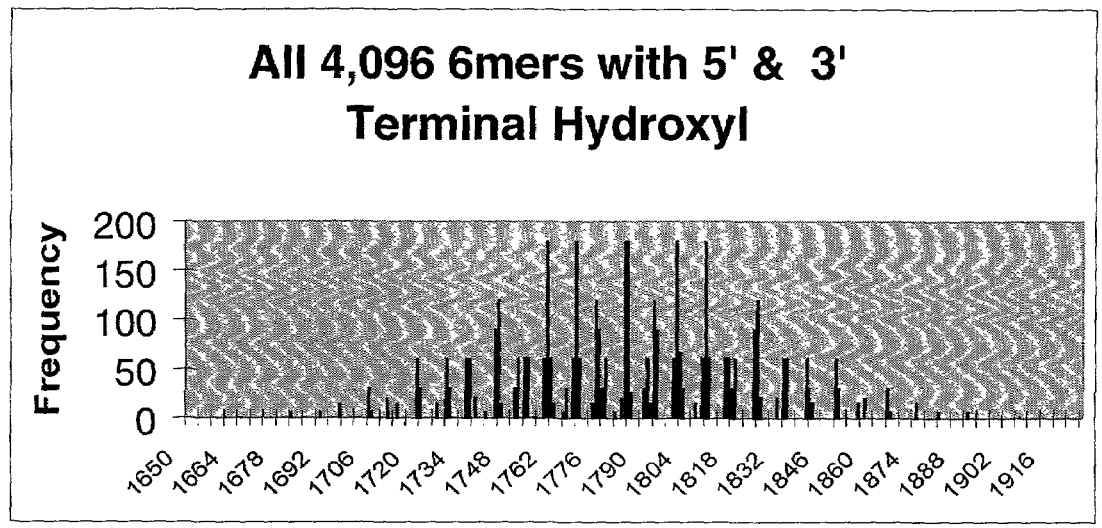
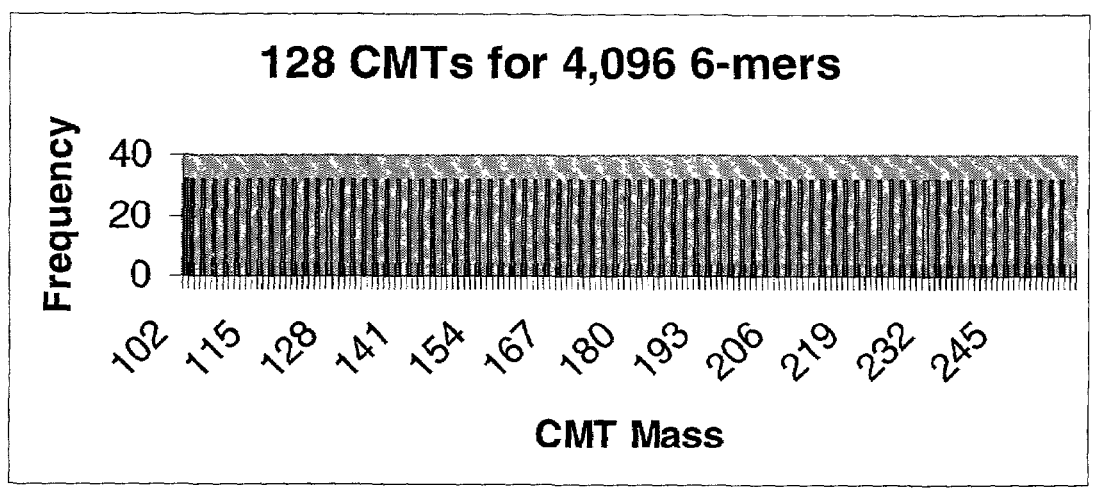

Nested set of overlapping X-mers

Nested set of semi-overlapping X-mers

Set of Non-overlapping X-mers

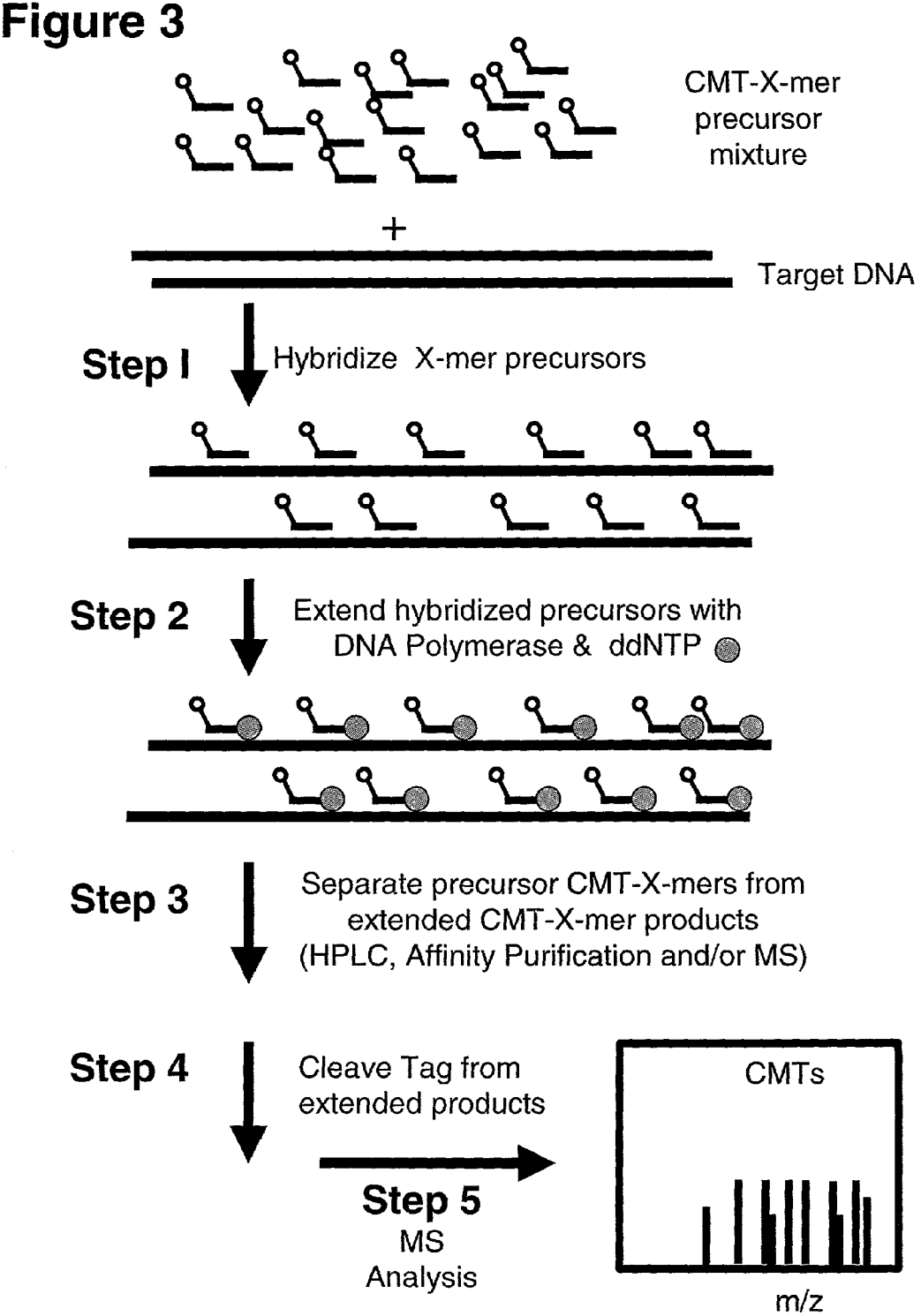

Figure 7

TACACATTGTCAAGGACGTACCCGCCGTACTTGGCCTCCGGGTAGGAGTGGTAGTAGTGTGAC

```
ATGTGTA
 TGTGTAA
  GTGTAAC
   TGTAACA
    GTAACAG
     TAACAGT
      AACAGTT
       ACAGTTC
        CAGTTCC
         AGTTCCT
          GTTCCTG
           TTCCTGC
            TCCTGCA
             CCTGCAT
              CTGCATG
               TGCATGG
                GCATGGG
                 CATGGGC
                  ATGGGCG
                   TGGGCGG
                    GGGCGGC
                     GGCGGCA
                      GCGGCAT
                       CGGCATG
                        GGCATGA
                         GCATGAA
                          CATGAAC
                           ATGAACC
                            TGAACCG
                             GAACCGG
                              AACCGGA
                               ACCGGAG
                                CCGGAGG
                                 CGGAGGC
                                  GGAGGCC
                                   GAGGCCC
                                    AGGCCCA
                                     GGCCCAT
                                      GCCCATC
                                       CCCATCC
                                        CCATCCT
                                         CATCCTC
                                          ATCCTCA
                                           TCCTCAC
                                            CCTCACC
                                             CTCACCA
                                              TCACCAT
                                               CACCATC
                                                ACCATCA
                                                 CCATCAT
                                                  CATCATC
                                                   ATCATCA
                                                    TCATCAC
                                                     CATCACA
                                                      ATCACAC
                                                       TCACACT
                                                        CACACTG
```

Figure 8
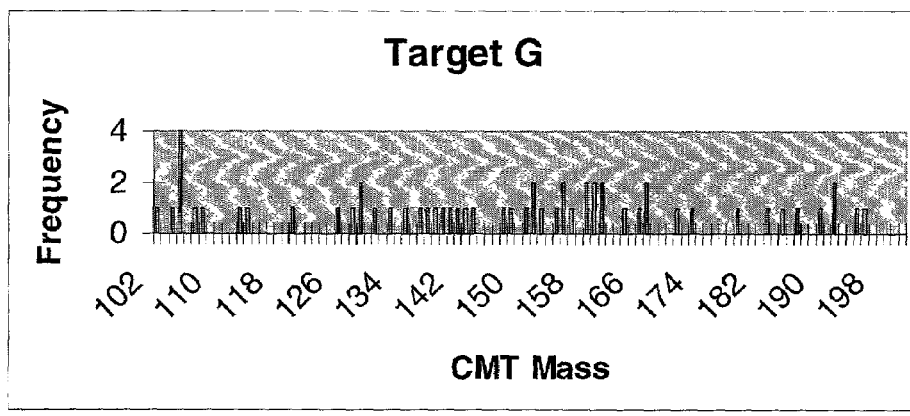
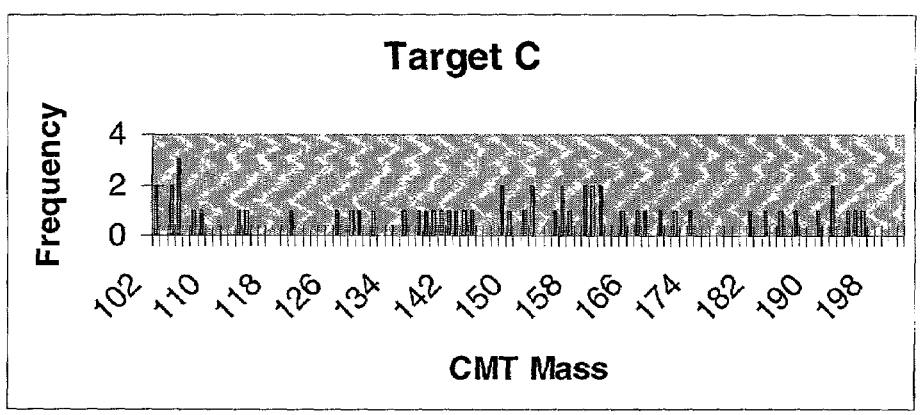
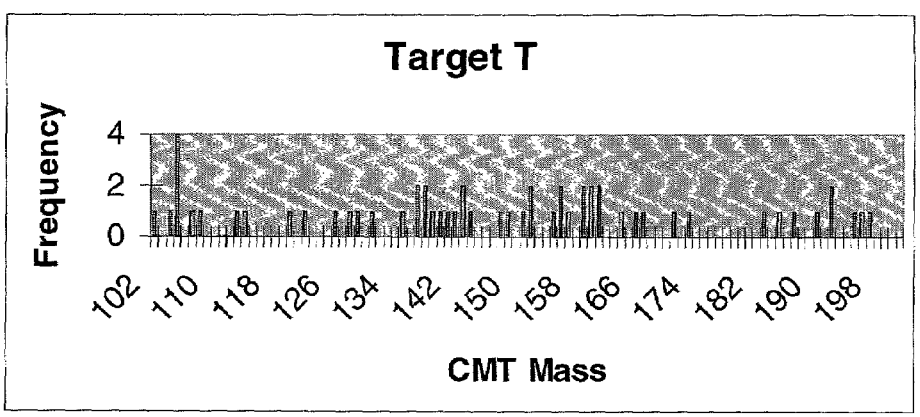

Figure 9
A
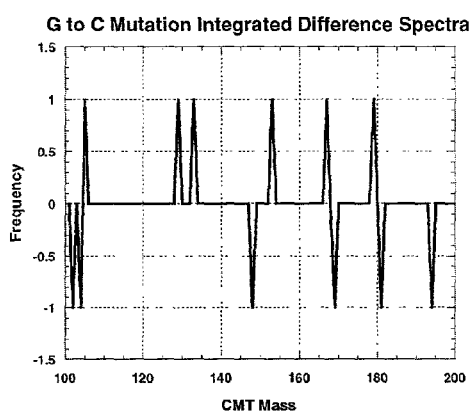
B
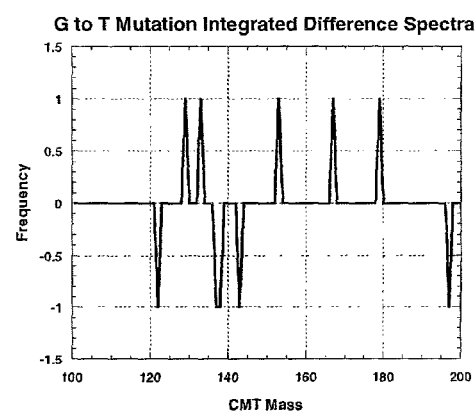
C
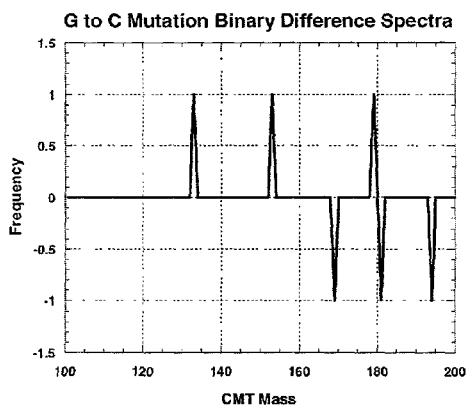
D
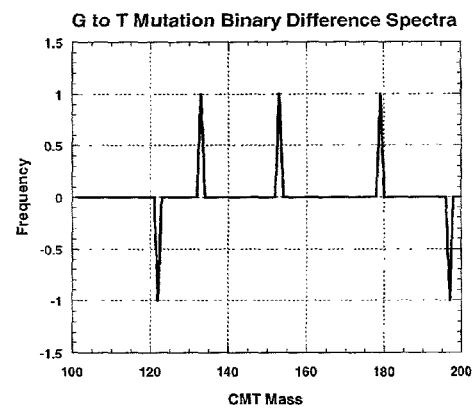

Figure 10
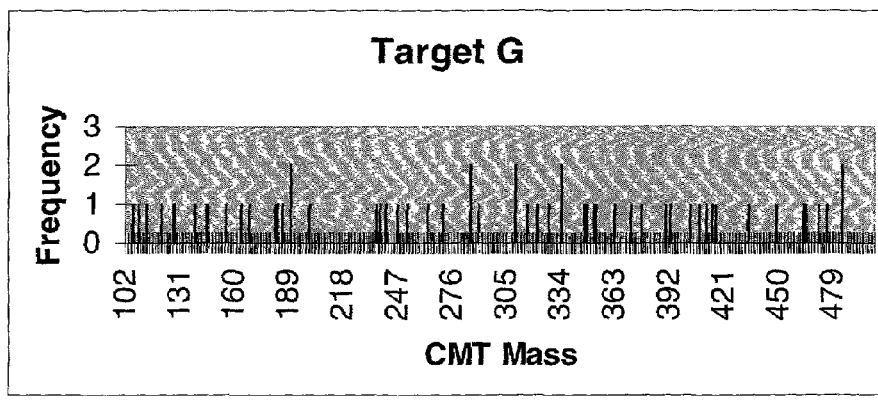
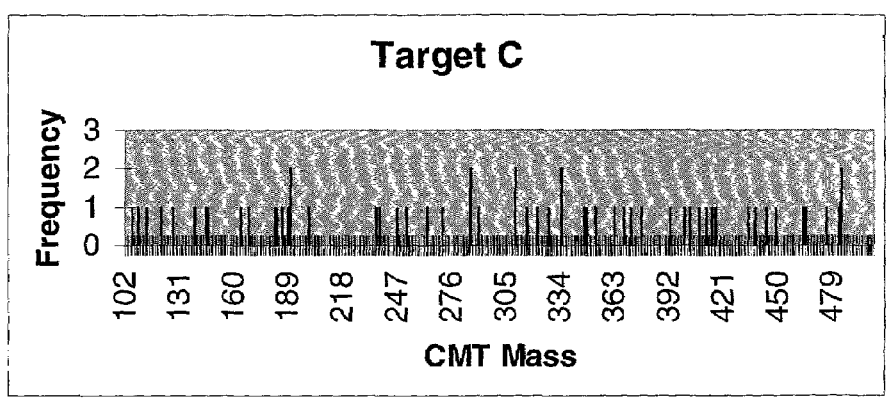
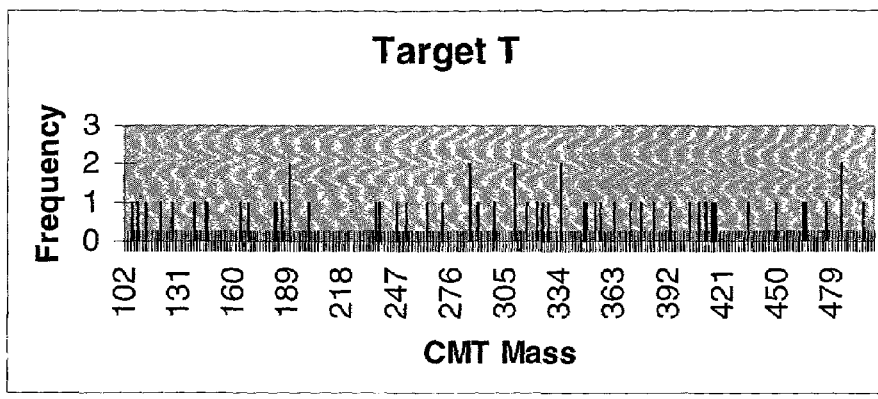

Figure 11
A
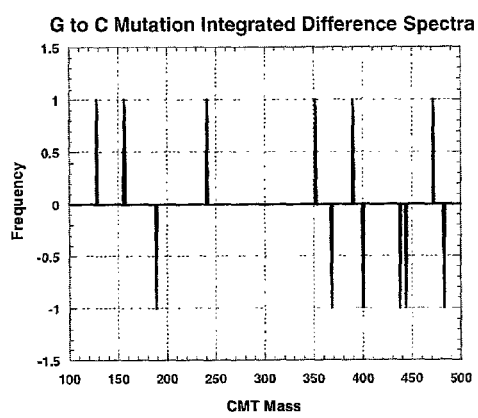
B
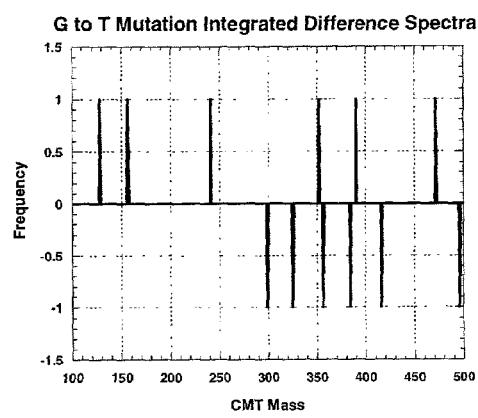
C
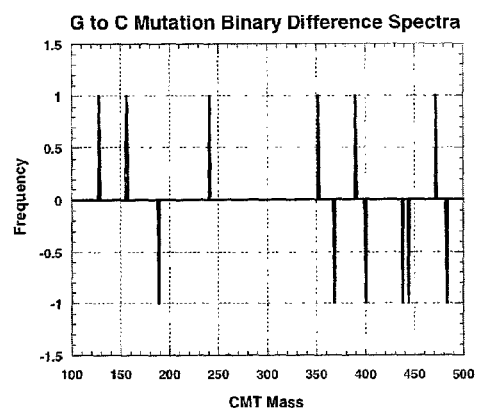
D
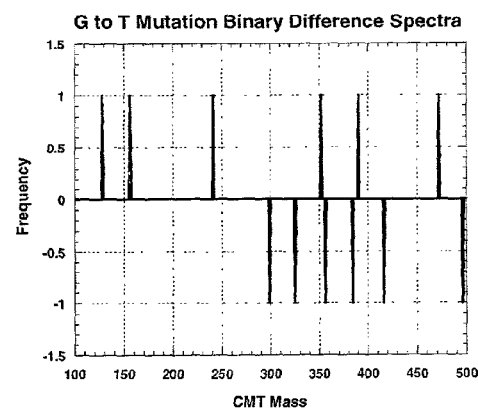

SEQUENCE LISTING

<160> NUMBER OF SEQ ID NOS: 1

<210> SEQ ID NO 1
<211> LENGTH: 63
<212> TYPE: DNA
<213> ORGANISM: Human

<400> SEQUENCE: 1
tacacattgt caaggacgta cccgccgtac ttggcctccg ggtaggagtg gtagtagtgt    60
gac    63

METHOD AND REAGENTS FOR ANALYZING THE NUCLEOTIDE SEQUENCE OF NUCLEIC ACIDS

RELATED APPLICATIONS

The present application claims priority under 35 U.S.C. §120 to U.S. Ser. No. 09/112,437 filed on Jul. 7, 1998, now U.S. Pat. No. 6,218,118 by Sampson et al. filed Jul. 9, 1998, and is a continuation-in-part of U.S. Ser. No. 09/112,437 which is incorporated by reference in its entirety.

FIELD OF THE INVENTION

This invention relates to methods and reagents for analyzing nucleotide sequences of nucleic acids via mass spectrometry, and more particularly relates to methods for analyzing nucleotide sequences employing reagents that are mixtures of oligonucleotide precursors having a high sequence-coverage complexity, and also having tags analyzable by mass spectrometry which are covalently linked to the oligonucleotides through cleavable bonds.

BACKGROUND OF THE INVENTION

Determining the nucleotide sequence of nucleic acids (DNA and RNA) is critical to understanding the function and control of genes and their relationship, for example, to disease discovery and disease management. Analysis of genetic information plays a crucial role in the biological experimentation. This has become especially true with regard to studies directed at understanding the fundamental genetic and environmental factors associated with disease and the effects of potential therapeutic agents on the cell. This paradigm shift has led to an increasing need within the life science industries for more sensitive, more accurate and higher-throughput technologies for performing analysis on genetic material obtained from a variety of biological sources.

Because sequencing the enormously large number of nucleic acids in each human cell is necessarily a time-consuming process, there is always a pressing need for faster and higher through-put analyses that do not sacrifice sensitivity and accuracy. A number of techniques have been developed, including, inter alia, electrophoresis, enzymatic and chemical analysis, array technology and mass spectrometry, to determine the nucleotide sequence of nucleic acids.

Electrophoretic Techniques

Slab or capillary polyacrylamide gel electrophoresis technologies, such as those employed in automated DNA sequencers, provide highly accurate de novo sequence information for relatively long (500-700 residues or bases) segments of DNA. Although electrophoresis-based techniques provide a great amount of information per sample, they require long sample preparation and set-up times and thereby limit throughput.

Enzymatic and Chemical Analysis

A number of enzymatic and chemical techniques exist to determine the de novo nucleotide sequence of nucleic acids. However, each technique has inherent limitations. For example, Maxam and Gilbert (*Proc. Natl. Acad. Sci. USA* 74:5460, 1977) disclose a chemical degradation approach and Sanger et al. (*Proc. Natl. Acad. Sci. USA* 74:5463, 1977) disclose a chain termination method using complementary strand primer extension. Each of these techniques utilizes four separate reaction mixtures to create a nested set of fragments differing by a single nucleotide in length, thus representing a complete nucleotide sequence. A resolution of the fragments based on their size and terminating nucleotide is carried out to determine the order of the fragments and hence the nucleotide sequence.

Single-stranded conformation polymorphism (SSCP) analysis is a useful technique for detecting relatively small differences among similar sequences. The technique is simple to implement, and when combined with multiple-dye detection or mass-tag methodologies, may be multiplexed and thereby improve throughput. However, like techniques that rely on detecting heteroduplexes, such as denaturing gradient gel electrophoresis (DGGE), chemical cleavage (CCM), enzymatic cleavage (using cleavase) of mismatches, and denaturing high performance liquid chromatography (DHPLC), the technique is only qualitative. More specifically, these techniques only reveals whether a mutation is present within the target nucleic acid, and provide minimal information about the identity and location of the mutation.

Other techniques employing ligase and polymerase extension assays are useful for determining whether a mutation is present at a defined location in an otherwise known target nucleic acid sequence. U.S. Pat. No. 4,988,617, for example, discloses a method for determining whether a mutation is present at a defined location in an otherwise known target nucleic acid sequence by assaying for the ligation of two natural oligonucleotides that are designed to hybridize adjacent to one another along the target sequence. U.S. Pat. No. 5,494,810 discloses a method that utilizes a thermostable ligase and the ligase chain reaction (LCR) to detect specific nucleotide substitutions, deletions, insertions and translocations within an otherwise known target nucleic acid sequence using only natural nucleic acids. U.S. Pat. No. 5,403,709 discloses a method for determining the nucleotide sequence by using another oligonucleotide as an extension and a third, bridging oligonucleotide to hold the first two together for ligation, and WO 97/35033 discloses methods for determining the identity of a nucleotide 3' to a defined primer using a polymerase extension assay. Although the assays may be performed with a relatively high throughput, they are sequence specific and, thus require a different set of reagents for each target to be analyzed.

U.S. Pat. Nos. 5,521,065, 4,883,750 and 5,242,794 (Whiteley, et al.) disclose methods of testing for the presence or absence of a target sequence in a mixture of single-stranded nucleic acid fragments. The method involves reacting a mixture of single-stranded nucleic acid fragments with a first probe that is complementary to a first region of the target sequence and with a second probe that is complementary to a second region of the target sequence. The first and second target regions are contiguous with one another. Hybridization conditions are used in which the two probes become stably hybridized to their associated target regions. Following hybridization, any of the first and second probes hybridized to contiguous first and second target regions are ligated, and the sample is subsequently tested for the presence of expected probe ligation product.

Array Technology

Techniques employing hybridization to surface-bound DNA probe arrays are useful for analyzing the nucleotide sequence of target nucleic acids. These techniques rely upon the inherent ability of nucleic acids to form duplexes via hydrogen bonding according to Watson-Crick base-pairing rules. In theory, and to some extent in practice, hybridization to surface-bound DNA probe arrays can provide a relatively large amount of information in a single experiment. For example, array technology has identified single nucleotide polymorphisms within relatively long (1,000 residues or bases) sequences (Kozal, M., et al., *Nature Med.* 7:753-759, July 1996). In addition, array technology is useful for some types of gene expression analysis, relying upon a comparative analysis of complex mixtures of mRNA target sequences (Lockart, D., et al., (1996) *Nat. Biotech.* 14, 1675-1680). Although array technologies offer the advantages of being reasonably sensitive and accurate when developed for specific applications and for specific sets of target sequences, they lack a generic implementation that can simultaneously be applied to multiple and/or different applications and targets. This is in large part due to the need for relatively long probe sequences, which are required to form and subsequently detect the probe/target duplexes. Moreover, this use of relatively long probes makes it difficult to interrogate single nucleotide differences due to the inherently small thermodynamic difference between the perfect complement and the single mismatch within the probe/target duplex. In addition, detection depends upon solution diffusion properties and hydrogen bonding between complementary target and probe sequences.

Mass Spectrometry Techniques

Mass spectrometry (MS) is a powerful tool for analyzing complex mixtures of compounds, including nucleic acids. In addition to accurately determining an intact mass, primary structure information can be obtained by several different MS strategies. The use of MS for DNA analysis has potential application to the detection of DNA modifications, DNA fragment mass determination, and DNA sequencing (see for example; Fields, G. B., *Clinical Chemistry* 43, 1108 (1997)). Both fast atom bombardment (FAB) and electrospray ionization (ESI) collision-induced dissociation/tandem MS have been applied for identification of DNA modification sites.

Although MS is a powerful tool for analyzing complex mixtures of related compounds, including nucleic acids, its utility for analyzing the sequence of nucleic acids is limited by available ionization and detection methods. For example, ESI spectrometry produces a distribution of highly charged ions having a mass-to-charge ratio in the range of commercially available quadrupole mass analyzers. While ESI is sensitive, requiring only femtomole quantities of sample, it relies on multiple charges to achieve efficient ionization and produces complex and difficult-to-interpret multiply-charged spectra for even simple nucleic acids.

Matrix-assisted laser desorption ionization (MALDI) used in conjunction with a time-of-flight (TOF) mass analyzer holds great potential for sequencing nucleic acids because of its relatively broad mass range, high resolution (n/$\Delta$m<1.0 at mass 5,000) and sampling rate (up to 1 sample/second). In one aspect MALDI offers a potential advantage over ESI and FAB in that biomolecules of large mass can be ionized and analyzed readily. Furthermore, in contrast to ESI, MALDI produces predominantly singly charged species.

However, in general, MALDI analysis of DNA may suffer from lack of resolution of high molecular weight DNA fragments, DNA instability, and interference from sample preparation reagents. Longer oligonucleotides can give broader, less intense signals, because MALDI imparts greater kinetic energies to ions of higher molecular weights. Although it may be used to analyze high molecular-weight nucleic acids, MALDI-TOF induces cleavage of the nucleic acid backbone, which further complicates the resulting spectrum. As a result, the lengths of nucleic acid sequences that may currently be analyzed via MALDI-TOF is limited to about 100 bases or residues. Wang et al. (WO 98/03684) have taken advantage of "in source fragmentation" and coupled it with delayed pulsed ion extraction methods for determining the sequence of nucleic acid analytes.

A number of methods have been disclosed that take advantage of standard sequencing methods for generating target fragments for analysis by mass spectroscopy. For example, U.S. Pat. No. 5,288,644 (Beavis, et al.); U.S. Pat. No. 5,547, 835 (Koster) and U.S. Pat. No. 5,622,824 (Koster) disclose methods for determining the sequence of a target nucleic acid using MALDI-TOF of ladders of the target produced either by exonuclease digestion or by standard Sanger sequencing methods. Beavis discusses a method for DNA sequencing utilizing different base-specific reactions to use different sets of DNA fragments to form a piece of DNA of unknown sequence. Each of the different sets of DNA fragments has a common origin and terminates at a particular base along the unknown sequence. The molecular weights of the DNA fragments in each of the different sets are determined by a MALDI mass spectrometer which is then used to deduce the nucleotide sequence of the DNA.

Koster utilizes the Sanger sequencing strategy and assembles the sequence information by analysis of the nested fragments obtained by base-specific chain termination via their different molecular masses using mass spectrometry such as MALDI or ESI mass spectrometry. This method has been coupled with a solid-phase sequencing approach in which the template is labeled with biotin and bound to streptavidin-coated magnetic beads. Using this method, it was possible to sequence exons 5 and 8 of p53 gene using 21 defined primers (Fu et al., *Nat. Biotechnol* 16, 381 (1998)). Throughput can be increased by introducing mass modifications in the oligonucleotide primer, chain-terminating nucleoside triphosphates and/or in the chain-elongating nucleoside triphosphates, as well as using integrated tag sequences that allow multiplexing by hybridization of tag specific probes with mass differentiated molecular weights (U.S. Pat. No. 5,547, 835). It is important to note, however, that all of these sequencing methods require either some prior knowledge of the target sequence or introduction of a known sequence to serve as the primer-binding site.

Efforts have been made to use mass spectrometry with enzymatic assays to determine the presence, location and identity of mutations in otherwise known sequences wherein at least some information is known a priori about the presence, location and/or identity of the mutation. U.S. Pat. No. 5,605,798, for example, discloses a method wherein a DNA primer that is complementary to a known target molecule in a region adjacent to the known region of interest is extended with a DNA polymerase in the presence of mass-tagged dideoxynucleotides. The identity of the mutation is then determined by analyzing the mass of the dideoxy-extended DNA primer. The multiplexing method is disclosed to be useful for simultaneously detecting all possible mutants/variants at a defined site by extending with a dideoxynucleotide and determining which specific dideoxynucleotide was incorporated.

Efforts have been made to address some of the aforementioned deficiencies with mass spectroscopic analyses of nucleic acids. For example, Gut (WO 96/27681) discloses methods for altering the charge properties of the phosphodiester backbone of nucleic acids in ways that make them more suitable for MS analyses. Methods for introducing modified nucleotides that stabilize the nucleic acid against fragmentation have also been described (Schneider and Chait, *Nucleic Acids Res*, 23, 1570 (1995), Tang et al., *J Am Soc Mass Spectrom*, 8, 218-224, 1997).

The use of non-cleavable mass tags has also been exploited to address some of the aforementioned deficiencies. For example, Japanese Patent No. 59-131909 discloses a mass spectrometer design that detects nucleic acid fragments separated by electrophoresis, liquid chromatography or high speed gel filtration, wherein atoms have been incorporated into the nucleic acids. The atoms, which normally do not occur in DNA, are sulfur, bromine, iodine, silver, gold, platinum, and mercury.

Cleavable mass tags have been exploited to circumvent some of the problems associated with MS analysis of nucleic acids. For example, Southern, et al. (PCT Application WO 95/04160) discloses an indirect method for analyzing the sequence of target nucleic acids using target-mediated ligation between a surface-bound DNA probe and cleavable mass-tagged oligonucleotides containing reporter groups using mass spectrometric techniques. The sequence to be determined is first hybridized to an oligonucleotide attached to a solid support. The solid support carrying the hybrids from above is incubated with a solution of coded oligonucleotide reagents that form a library comprising all sequences of a given length. Ligase is introduced so that the oligonucleotide on the support is ligated to the member of the library that is hybridized to the target adjacent the oligonucleotide. Non-ligated reagents are removed by washing. A linker that is part of the member of the library ligated to the oligonucleotide is broken to detach a tag, which is recovered and analyzed by mass spectrometry.

A common focus of the above technologies is to provide methods for increasing the number of target sites (either intra- or inter-target) that can be interrogated in a single determination where some portion of the target sequence is known. This multiplexing theme is either directly stated or implied in the teachings of the above patent applications. The use of more than one oligonucleotide as either a hybridization probe or primer for extension or ligation is defined by the sequence surrounding the site of interest and, therefore, the specific application. Thus, with the exception of the mass-tag technology disclosed by Southern, the oligonucleotide reagents described above are not generic in terms of target sequence, but must be generated for each defined application. As such, the number of distinct oligonucleotides used in a multiplexed interrogation is generally only a small subset of the theoretical sequence-complete set. This ratio of actual sequence coverage provided by a particular oligonucleotide mixture to the theoretical coverage provided by the sequence-complete set is defined as the mixture coverage complexity (see discussion below). For example, in many of the methods described (i.e., U.S. Pat. No. 5,605,798, WO 92/15712, and WO 97/35033), the probe lengths vary from about 8 to 20 nucleotides depending upon the specific application and method of detection. The number of probes in a sequence-complete set can be described by the equation $4^L$ where L equals the length of the probes. Thus for 8-mer probes, the sequence-complete set has to $4^8$ or 65,536 members. If the number of interrogation sites in the multiplexed determination is about 500, which is a reasonable upper boundary for the number of oligonucleotide probes in a single determination for the types of technologies described above, then the mixture coverage complexity (see discussion below) of the interrogating 8-mer probe mixture would be equal to 500/65,536 or approximately 1/130. In most cases, however, the probes are 15-20 nucleotides in length. While this increased length ensures specificity of the probe for a defined target sequence, it makes the mixture coverage complexity of the probe mixture significantly smaller. Thus, it is clear that for the types of multiplexing methods and applications described above, the interrogating oligonucleotide mixtures are not designed to be sequence complete with regard to target sequence coverage and could not therefore be considered generic reagents.

The object of many array-based sequencing techniques is to determine the "short word" content, i.e., all of the oligonucleotide subsequences present, in the target nucleic acid sequence. For example, in techniques employing hybridization to surface-bound DNA probe arrays, a set of oligonucleotides of a particular length are arranged in spatially distinct locations on a substrate to form an array, and the target sequence is permitted to hybridize to the array (see for example, U.S. Pat. No. 5,202,231, U.S. Pat. No. 5,492,806, and U.S. Pat. No. 5,695,940). The target sequence will bind at locations that contain a short word complementary to one of the short words in its sequence. Others have disclosed methods for probing surface-bound targets with a sequential set of oligonucleotide probes (see for example, U.S. Pat. No. 5,202,231, U.S. Pat. No. 5,492,806, and U.S. Pat. No. 5,695,940). By identifying the hybridization locations, or knowing the identity of the probing oligonucleotide via a fluorescence measurement or the like, the precise short word content of the target nucleic acid sequence may theoretically be determined. This information can then be used to reconstruct the sequence of the target nucleic acid (see for example; Pevzner, P. A., *J. Biomolecular Structure Dynamics* 7, 63 (1989), Pevzner P. A., et al., *J. Biomolecular Structure Dynamics* 9, 399 (1991), Ukkonen, E., *Theoretical Computer Science* 92, 191 (1992)). It is important to emphasize, however, that relatively sequence-complete sets of oligonucleotide probes are required in order to generically determine the short word content an unknown target.

Techniques that identify the short-word content of the target nucleic acid sequence are useful for applications such as de novo sequencing, re-sequencing, mutation detection and mutational change detection. As the length of the target sequence increases, the success rate or success rate with which the analysis may be carried out decreases. Because some of the applications require only qualitative information (e.g., mutation detection), the success rate may typically be higher than the success rate for an application requiring quantitative information, e.g., de novo sequencing. For example, the presence of a few short word repeats would severely reduce the success rate for de novo sequencing, but would have a reduced effect on the success rate for mutation detection. In other applications, substantial prior information is available to assist in the interpretation of the short-word content, thus increasing the success rate of the results.

The purpose of the present invention is to determine the short word content of a target nucleic acid sequence using mass spectroscopy. However, the success rate of such an analysis is expected to be relatively low because the presence of a particular mass in the mass spectrum only reveals that one of many possible nucleic acid sequences is present. For example, using only natural nucleotides, the sequence of GGCTTTA is indistinguishable by mass from the sequence of GCTTTAG, and the presence of a mass peak at 2,142 atomic mass units merely reveals that at least one nucleic acid sequence with 3 T's, 2 G's and 1 A and 1 C is present in the mixture. The ambiguity is further confounded by mass coincidences. For example, the mass peak at 2,193 may contain contributions from nucleic acid sequences containing 6 A's and 1 T or 1 A, 2 C's, 3 G's and 1 T. Therefore, this is a great need for rapid analytical methods that reduce ambiguity inherent in data from MS analysis of nucleic acids.

SUMMARY OF THE INVENTION

The present invention is directed to reagents and methods for recapitulating a target nucleic acid in the short-word form that can be analyzed by high-resolution mass spectrometry techniques. The methods and reagents utilize generic oligonucleotide precursor mixtures (X-mer precursor mixtures) comprising tags covalently attached through cleavable bonds, and enzymatic processes to alter the length, and concomitantly the mass, of only those X-mer precursors within a defined mixture that are complementary to the target nucleic acid and therefore have hybridized to the target nucleic acid to permit enzymatic processing.

In one aspect, the present invention is a mixture or a set of sub-mixtures comprising nucleic acids and tags covalently attached to the nucleic acids through cleavable linkers for direct mass spectral analysis of the tags after release by cleavage of the linkers, where the tags are distinguishable by mass spectrometry and are assigned to known sequences of X-mer precursors. The mixture comprises X-mer precursors having a minimum length of 3 nucleotides. The minimum mixture coverage complexity ($CC_M$) of the mixture (or minimum composite mixture coverage complexity of the set of sub-mixtures) is 56 divided by N, where N is the number of distinct X-mers in the mixture. The length of the X-mer precursors can be selected independently for each X-mer precursor. Each of the X-mer precursors in the mixture is represented by a single chemical species. Each sub-mixture in the set has a reduced mixture coverage complexity relative to the composite mixture coverage complexity. Further, each sub-mixture comprises a plurality of X-mer precursors.

In another aspect, the present invention provides a method of analyzing a target nucleic acid sequence. In the method, a mixture of X-mer precursors (or a sub-mixture from a set of sub-mixtures) comprises tags covalently attached to the nucleic acids through cleavable linkers for direct mass spectral analysis of the tags after release by cleavage of the linkers, where the tags are distinguishable by mass spectrometry and are assigned to known sequences of X-mer precursors. The mixture comprises X-mer precursors having a minimum length of 3 nucleotides. The minimum mixture coverage complexity of the mixture (or minimum composite mixture coverage complexity of the set of sub-mixtures) is 56 divided by N, where N is the number of distinct X-mers in the mixture. The length of the X-mer precursors can be selected independently for each X-mer precursor. Each of the X-mer precursors in the mixture is represented by a single chemical species. Each sub-mixture in the set has a reduced mixture coverage complexity relative to the composite mixture coverage complexity. Further, each sub-mixture comprises a plurality of X-mer precursors.

The X-mer precursors in the mixture are hybridized to the target nucleic acid sequences producing hybrids. The hybrids are processed to alter the mass of the X-mer precursor portions of the hybrids in a target sequence-mediated reaction. The reaction captures hybridization events between X-mer precursors and their complementary sequences within a target nucleic acid by altering the mass of the X-mer precursor. As a result, sequence information on the target nucleic acids is recapitulated by the mass-altered X-mer precursors. Therefore, mass-altered X-mer precursors are then separated from the unaltered (i.e. unhybridized) X-mer precursors for analysis.

After separation, the tags are released from the mass-altered nucleic acid X-mer precursors by cleavage of the linkers. The isolated tags, which may be purified, are then analyzed by mass spectrometry. Additionally or alternatively, the step of cleaving the linkers and the step of analysis by mass spectrometry are performed in the same step. Since tags are assigned and linked to X-mer precursors whose nucleotide sequences are known, information obtained from mass spectral analysis is then used to determine the nucleotide sequence of the target nucleic acid.

In one embodiment, the present invention is a kit for carrying out the above method. The kit comprises a mixture or set of sub-mixtures as described above, an enzyme having DNA polymerase activity, and a multiplicity of chain-terminating nucleotide triphosphates.

BRIEF DESCRIPTION OF THE DRAWINGS

FIG. 1 is a mass histogram for (A) all 4,096 natural 6-mers and for (B) the cleavable mass tags (CMTs) where 128 CMTs having masses ranging from 101 to 356 in 2 a.m.u. increments are arbitrarily assigned to all 4,096 6-mers.

FIG. 3 is a diagram outlining the steps of the Polymerase Extension Assay (PEA) using cleavable mass tags (CMTs) (CMT-PEA).

FIG. 7 depicts a nested set of overlapping 7-mer PEA products corresponding to the 62 nucleotide fragment of the wild type p53 sequence.

FIG. 8 depicts mass spectra of CMT-PEA analysis for (A) the wild type; (B) G2451C; and (C) G2451T p53 mutants within the 62 nucleotide target fragment using 100 CMTs arbitrarily assigned to all 4,096 6-mers.

FIG. 9 depicts an integrated (A & B) and binary transformed (C & D) difference spectra for the wild type and the G2451C and G2451T p53 mutants.

FIG. 10 depicts mass spectra of CMT-PEA analysis for (A) the wild type; (B) G2451C; and (C) G2451T p53 mutant within the 62 nucleotide target fragment using 400 CMTs arbitrarily assigned to 4,096 6-mers.

FIG. 11 depicts integrated (A & B) and binary transformed (C & D) difference spectra for the wild type and the G2451C and G2451 T p53 mutants.

DETAILED DESCRIPTION OF THE INVENTION

Definitions

Figure 2A:
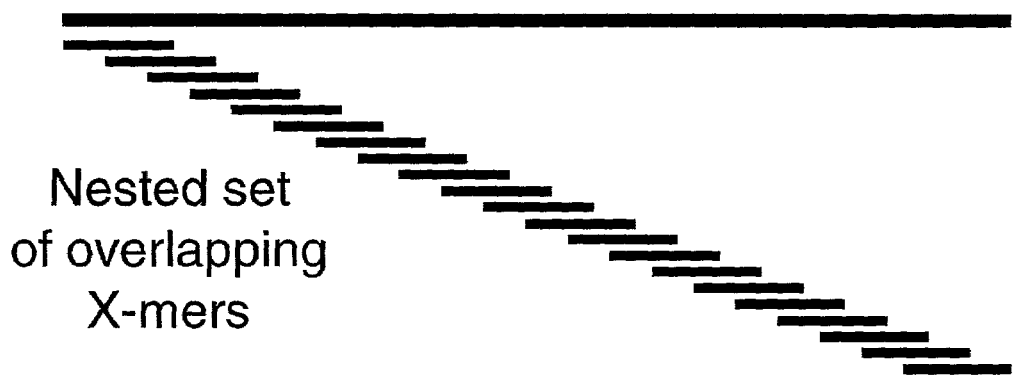
FIG. 2 is a recapitulation of target sequence by different types of sets of short X-mers. A) Nested set of overlapping X-mers; (B) Nested set of semi-overlapping X-mers; (C) Set of Non-overlapping X-mers.

In this specification and in the claims that follow, reference will be made to a number of terms that shall be defined to have the following meaning:

The term "polynucleotide" or "nucleic acid" refers to a compound or composition that is a polymeric nucleotide or nucleic acid polymer. The polynucleotide may be a natural compound or a synthetic compound. The polynucleotide can have from about 20 to 5,000,000 or more nucleotides. The larger polynucleotides are generally found in the natural state. In an isolated state the polynucleotide can have about 30 to 50,000 or more nucleotides, usually about 100 to 20,000 nucleotides, more frequently 500 to 10,000 nucleotides. It is thus obvious that isolation of a polynucleotide from the natural state often results in fragmentation. It may be useful to fragment longer target nucleic acid sequences, particularly RNA, prior to hybridization to reduce competing intramolecular structures.

The polynucleotides include nucleic acids, and fragments thereof, from any source in purified or unpurified form including DNA (dsDNA and ssDNA) and RNA, including tRNA, mRNA, rRNA, mitochondrial DNA and RNA, chloroplast DNA and RNA, DNA/RNA hybrids, or mixtures thereof, genes, chromosomes, plasmids, cosmids, the genomes of biological material such as microorganisms, e.g., bacteria, yeasts, phage, chromosomes, viruses, viroids, molds, fungi, plants, animals, humans, and the like. The polynucleotide can be only a minor fraction of a complex mixture such as a biological sample. Also included are genes, such as hemoglobin gene for sickle-cell anemia, cystic fibrosis gene, oncogenes, cDNA, and the like.

The polynucleotide can be obtained from various biological materials by procedures well known in the art. The polynucleotide, where appropriate, may be cleaved to obtain a fragment that contains a target nucleotide sequence, for example, by shearing or by treatment with a restriction endonuclease or other site-specific chemical cleavage method.

For purposes of this invention, the polynucleotide, or a cleaved fragment obtained from the polynucleotide, will usually be at least partially denatured or single stranded or treated to render it denatured or single stranded. Such treatments are well known in the art and include, for instance, heat or alkali treatment, or enzymatic digestion of one strand. For example, dsDNA can be heated at 90 to 100 degrees C. for a period of about 1 to 10 minutes to produce denatured material.

The nucleic acids may be generated by in vitro replication and/or amplification methods such as the Polymerase Chain Reaction (PCR), asymmetric PCR, the Ligase Chain Reaction (LCR) and so forth. The nucleic acids may be either single-stranded or double-stranded. Single-stranded nucleic acids are preferred because they lack complementary strands that compete for the oligonucleotide precursors during the hybridization step of the method of the invention.

The phrase "target nucleic acid sequence" refers to a sequence of nucleotides to be identified, detected or otherwise analyzed, usually existing within a portion or all of a polynucleotide. In the present invention the identity of the target nucleotide sequence may or may not be known. The identity of the target nucleotide sequence may be known to an extent sufficient to allow preparation of various sequences hybridizable with the target nucleotide sequence and of oligonucleotides, such as probes and primers, and other molecules necessary for conducting methods in accordance with the present invention and so forth. Determining the sequence of the target nucleic acid includes in its definition, determining the sequence of the target nucleic acid or sequences within regions of the target nucleic acid to determine the sequence de novo, to resequence, and to detect mutations and/or polymorphisms.

The target sequence usually contains from about 30 to 5,000 or more nucleotides, preferably 50 to 1,000 nucleotides. The target nucleotide sequence is generally a fraction of a larger molecule or it may be substantially the entire molecule such as a polynucleotide as described above. The minimum number of nucleotides in the target nucleotide sequence is selected to assure that the presence of a target polynucleotide in a sample is a specific indicator of the presence of polynucleotide in a sample. The maximum number of nucleotides in the target nucleotide sequence is normally governed by several factors: the length of the polynucleotide from which it is derived, the tendency of such polynucleotide to be broken by shearing or other processes during isolation, the efficiency of any procedures required to prepare the sample for analysis (e.g. transcription of a DNA template into RNA) and the efficiency of identification, detection, amplification, and/or other analysis of the target nucleotide sequence, where appropriate.

The term "oligonucleotide" refers to a polynucleotide, usually single stranded, usually a synthetic polynucleotide but may be a naturally occurring polynucleotide. The length of an oligonucleotide is generally governed by the particular role thereof, such as, for example, probe, primer, X-mer, and the like. Various techniques can be employed for preparing an oligonucleotide. Such oligonucleotides can be obtained by biological synthesis or by chemical synthesis. For short oligonucleotides (up to about 100 nucleotides), chemical synthesis will frequently be more economical as compared to the biological synthesis. In addition to economy, chemical synthesis provides a convenient way of incorporating low molecular weight compounds and/or modified bases during specific synthesis steps. Furthermore, chemical synthesis is very flexible in the choice of length and region of the target polynucleotide binding sequence. The oligonucleotide can be synthesized by standard methods such as those used in commercial automated nucleic acid synthesizers. Chemical synthesis of DNA on a suitably modified glass or resin can result in DNA covalently attached to the surface. This may offer advantages in washing and sample handling. Methods of oligonucleotide synthesis include phosphotriester and phosphodiester methods (Narang, et al. (1979) Meth. Enzymol 68:90) and synthesis on a support (Beaucage, et al. (1981) Tetrahedron Letters 22:1859-1862) as well as phosphoramidite techniques (Caruthers, M. H., et al., "Methods in Enzymology," Vol. 154, pp. 287-314 (1988)) and others described in "Synthesis and Applications of DNA and RNA," S. A. Narang, editor, Academic Press, New York, 1987, and the references contained therein. The chemical synthesis via a photolithographic method of spatially addressable arrays of oligonucleotides bound to glass surfaces is described by A. C. Pease, et al. (*Proc. Nat. Acad. Sci. USA* 91:5022-5026, 1994).

The term "X-mer" refers to an oligonucleotide that has a defined length, which is usually a sequence of at least 3 nucleotides, preferably, 4 to 14 nucleotides, and usually 5 to 7 nucleotides in length.

The phrase "X-mer precursors", sometimes referred to as "oligonucleotide precursors" refers to a nucleic acid sequence that is complementary to a portion of the target nucleic acid sequence. The oligonucleotide precursors are sequences of nucleoside monomers joined by phosphorus linkages (e.g., phosphodiester, alkyl and aryl-phosphate, phosphorothioate, phosphotriester), or non-phosphorus linkages (e.g., peptide, sulfamate and others). They may be natural or synthetic molecules of single-stranded DNA and single-stranded RNA with circular, branched or linear shapes and optionally including domains capable of forming stable secondary structures (e.g., stem-and-loop and loop-stem-loop structures). The oligonucleotide precursors contain a 3'-end and a 5'-end. The phrase will be denoted by ω.

The term "mixture" refers to a physical mixture of two or more substances. The term will be denoted by Ω.

The phrase "oligonucleotide probe" refers to an oligonucleotide employed to bind to a portion of a polynucleotide such as another oligonucleotide or a target nucleotide sequence. The design and preparation of the oligonucleotide probes are generally dependent upon the sequence to which they bind.

The phrase "oligonucleotide primer(s)" refers to an oligonucleotide that is usually employed in a chain extension on a polynucleotide template such as in, for example, an amplification of a nucleic acid. The oligonucleotide primer is usually a synthetic nucleotide that is single stranded, containing a sequence at its 3' end that is capable of hybridizing with a defined sequence of the target polynucleotide. Normally, an oligonucleotide primer has at least 80%, preferably 90%, more preferably 95%, most preferably 100%, complementarity to a defined sequence or primer binding site. The number of nucleotides in the hybridizable sequence of an oligonucleotide primer should be such that stringency conditions used to hybridize the oligonucleotide primer will prevent excessive random nonspecific hybridization. Usually, the number of nucleotides in the oligonucleotide primer will be at least as great as the defined sequence of the target polynucleotide, namely, at least ten nucleotides, preferably at least 15 nucleotides, and generally from about 10 to 200, preferably 20 to 50, nucleotides.

The phrase "nucleoside triphosphates" refers to nucleosides having a 5'-triphosphate substituent. The nucleosides are pentose sugar derivatives of nitrogenous bases of either purine or pyrimidine derivation, covalently bonded to the 1'-carbon of the pentose sugar, which is usually a deoxyribose or a ribose. The purine bases include adenine (A), guanine (G), inosine (I), and derivatives and analogs thereof. The pyrimidine bases include cytosine (C), thymine (T), uracil (U), and derivatives and analogs thereof. Nucleoside triphosphates include deoxyribonucleoside triphosphates such as the four common deoxyribonucleoside triphosphates dATP, dCTP, dGTP and dTTP and ribonucleoside triphosphates such as the four common triphosphates rATP, rCTP, rGTP and rUTP. The term "nucleoside triphosphates" also includes derivatives and analogs thereof, which are exemplified by those derivatives that are recognized and polymerized in a similar manner to the underivatized nucleoside triphosphates.

The term "nucleotide" or "nucleotide base" or "base" refers to a base-sugar-phosphate combination that is the monomeric unit of nucleic acid polymers, i.e., DNA and RNA. The term as used herein includes modified nucleotides as defined below. In general, the term refers to any compound containing a cyclic furanoside-type sugar (β-D-ribose in RNA and β-D-2'-deoxyribose in DNA), which is phosphorylated at the 5' position and has either a purine or pyrimidine-type base attached at the C-1' sugar position via a β-glycosol C1'-N linkage. These terms are interchangeable and will be denoted by a b. The nucleotide may be natural or synthetic, including a nucleotide that has been mass-modified including, inter alia, nucleotides having modified nucleosides with modified bases (e.g., 5-methyl cytosine) and modified sugar groups (e.g., 2'-O-methyl ribosyl, 2'-O-methoxyethyl ribosyl, 2'-fluoro ribosyl, 2'-amino ribosyl, and the like).

The term "DNA" refers to deoxyribonucleic acid.

The term "RNA" refers to ribonucleic acid.

The term "natural nucleotide" refers to those nucleotides that form the fundamental building blocks of cellular DNA, which are defined to include deoxycytidylic acid (pdC), deoxyadenylic acid (pdA), deoxyguanylic acid (pdG) and deoxythymidylic acid (pdT) and the fundamental building blocks of cellular RNA which are defined to include deoxycytidylic acid (pdC), deoxyadenylic acid (pdA), deoxyguanylic acid (pdG) and deoxyuridylic acid (pdU). pdU is considered to be a natural equivalent of pdT.

The term "natural nucleotide base" refers to purine- and pyrimidine-type bases found in cellular DNA and include cytosine (C), adenine (A), guanine (G) and thymine (T) and in cellular RNA and include cytosine (C), adenine (A), guanine (G) and uracil (U). U is considered a natural equivalent of T.

The phrase "modified nucleotide" refers to a unit in a nucleic acid polymer that contains a modified base, sugar or phosphate group, or that incorporates a non-nucleotide moiety in its structure. The modified nucleotide can be produced by a chemical modification of the nucleotide either as part of the nucleic acid polymer or prior to the incorporation of the modified nucleotide into the nucleic acid polymer. For example, the methods mentioned above for the synthesis of an oligonucleotide may be employed. In another approach a modified nucleotide can be produced by incorporating a modified nucleoside triphosphate into the polymer chain during an amplification reaction. Examples of modified nucleotides, by way of illustration and not limitation, include dideoxynucleotides, derivatives or analogs that are biotinylated, amine modified, alkylated, fluorophor-labeled, and the like and also include phosphorothioate, phosphite, ring atom modified derivatives, and so forth.

The phrase "Watson-Crick base pairing" refers to the hydrogen bonding between two bases, with specific patterns of hydrogen bond donors and acceptors having the standard geometries defined in "Principles of Nucleic Acid Structure"; Wolfram Saenger, Springer-Verlag, Berlin (1984).

The phrase "base-pairing specificity" of a nucleotide base b refers to the number of natural nucleotide bases with which the base will form Watson-Crick base pairs. The term will be denoted by $S_{bp}(b)$. For example, the $S_{bp}(b)$ for the four natural nucleotides are as follows; $S_{bp}(A)=1$, $S_{bp}(G)=1$, $S_{bp}(C)=1$, and $S_{bp}(T)=1$.

The phrase "natural complement of a nucleotide" refers to the natural nucleotide with which a nucleotide most favorably forms a base pair according to the Watson-Crick base pairing rules. If the nucleotide can base pair with equal affinity with more than one natural nucleotide, or most favorably pairs with different natural nucleotides in different environments, then the nucleotide is considered to have multiple natural nucleotide complements.

The phrase "natural equivalent of a nucleotide" refers to the natural complement of the natural complement of the nucleotide. In cases where a nucleotide has multiple natural complements, then it is considered to have multiple natural equivalents.

The phrase "natural equivalent of an oligonucleotide precursor" refers to an oligonucleotide precursor in which each nucleotide has been replaced with its natural nucleotide equivalent. In cases where one or more of the original nucleotides has multiple natural equivalents, then the oligonucleotide precursors will be considered to have multiple natural equivalents, with the equivalents being chosen from all of the possible combinations of replacements. The phrase is denoted by NE(ω).

The term "nucleoside" refers to a base-sugar combination or a nucleotide lacking a phosphate moiety.

"Chain-terminating nucleoside triphosphate" is a nucleoside triphosphate that is capable of being added to an oligonucleotide primer in a chain extension reaction but is incapable of under going chain extension. Examples by way of illustration and not limitation include the four standard dideoxynucleotide triphosphates, mass-modified dideoxynucleotide triphosphate analogues, thio analogs of natural and mass-modified dideoxynucleotide triphosphates, arabanose, 3'-amino, 3'-azido, 3'-fluoro derivatives and the like.

The phrase "dideoxynucleoside triphosphate" refers to and includes the four natural dideoxynucleoside triphosphates (ddATP, ddGTP, ddCTP and ddTTP for DNA and ddATP, ddGTP, ddCTP and ddUTP for RNA) and mass-modified dideoxynucleoside triphosphates. The term may be denoted by ddNTP.

The phrase "extension nucleoside triphosphates" refers to and includes natural deoxynucleoside triphosphates, modified deoxynucleotide triphosphates, mass-modified deoxynucleoside triphosphates, 5'($\alpha$)-phosphothioate, and 5'-N ($\alpha$-phosphoramidate) analogs of natural and mass-modified deoxy and ribonucleoside triphosphates and the like, such as those disclosed in U.S. Pat. No. 5,171,534 and U.S. Pat. No. 5,547,835, the relevant portions of which are incorporated herein by reference.

The phrase "nucleotide polymerase" refers to a catalyst, usually an enzyme, for forming an extension of a polynucleotide along a DNA or RNA template where the extension is complementary thereto. The nucleotide polymerase is a template dependent polynucleotide polymerase and utilizes nucleoside triphosphates as building blocks for extending the 3'-end of a polynucleotide to provide a sequence complementary with the polynucleotide template. Usually, the catalysts are enzymes, such as DNA polymerases, for example, prokaryotic DNA polymerase (I, II, or III), T4 DNA polymerase, T7 DNA polymerase, E. coli DNA polymerase (Klenow fragment, 3'-5' exo-), reverse transcriptase, Vent DNA polymerase, Pfu DNA polymerase, Taq DNA polymerase, Bst DNA polymerase, and the like, or RNA polymerases, such as T3 and T7 RNA polymerases. Polymerase enzymes may be derived from any source such as cells, bacteria such as E. coli, plants, animals, virus, thermophilic bacteria, and so forth.

"Amplification" of nucleic acids or polynucleotides is any method that results in the formation of one or more copies of a nucleic acid or polynucleotide molecule (exponential amplification) or in the formation of one or more copies of only the complement of a nucleic acid or polynucleotide molecule (linear amplification). Methods of amplification include the polymerase chain reaction (PCR) based on repeated cycles of denaturation, oligonucleotide primer annealing, and primer extension by thermophilic template dependent polynucleotide polymerase, resulting in the exponential increase in copies of the desired sequence of the polynucleotide analyte flanked by the primers. The two different PCR primers, which anneal to opposite strands of the DNA, are positioned so that the polymerase catalyzed extension product of one primer can serve as a template strand for the other, leading to the accumulation of a discrete double stranded fragment whose length is defined by the distance between the 5' ends of the oligonucleotide primers. The reagents for conducting such an amplification include oligonucleotide primers, a nucleotide polymerase and nucleoside triphosphates such as, e.g., deoxyadenosine triphosphate (dATP), deoxyguanosine triphosphate (dGTP), deoxycytidine triphosphate (dCTP) and deoxythymidine triphosphate (dTTP). Other methods for amplification include amplification of a single stranded polynucleotide using a single oligonucleotide primer, the ligase chain reaction (LCR), the nucleic acid sequence based amplification (NASBA), the Q-beta-replicase method, and 3SR.

The terms "hybridization (hybridizing)" and "binding" in the context of nucleotide sequences are used interchangeably herein. The ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Increased stringency is achieved by elevating the temperature, increasing the ratio of co-solvents, lowering the salt concentration, and the like. Hybridization also includes in its definition the transient hybridization of two complementary sequences. It is understood by those skilled in the art that non-covalent binding between two molecules, including nucleic acids, obeys the laws of mass action. Therefore, for purposes of the present invention, hybridization between two nucleotide sequences for a length of time that permits primer extension and/or ligation is within the scope of the invention.

The term "complementary," "complement," or "complementary nucleic acid sequence" refers to the nucleic acid strand that is related to the base sequence in another nucleic acid strand by the Watson-Crick base-pairing rules. In general, two sequences are complementary when the sequence of one can bind to the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence. RNA sequences can also include complementary G/U or U/G basepairs.

The term "hybrid" refers to a double-stranded nucleic acid molecule formed by hydrogen bonding between complementary nucleotides. The term "hybridize" refers to the process by which single strands of nucleic acid sequences form double-helical segments through hydrogen bonding between complementary nucleotides.

The term "mass-modified" refers to a nucleic acid sequence whose mass has been changed either by an internal change, i.e., by addition, deletion, or substitution of a chemical moiety, to its chemical structure or by an external change, i.e., by the addition of a chemical moiety (atom or molecule) attached covalently, to its chemical structure. The chemical moiety is therefore referred to as a mass-modifying moiety.

The phrase "mass number of an atom" refers to the nucleon number of the most common isotope of the element of interest.

The reported mass for all nucleic acids (i.e. nucleotides, nucleotide precursors, oligonucleotides, X-mer and X-mer products) is calculated using the mass numbers for the most abundant isotopes of the constituent atoms (i.e. C12, N14, H1, O16, P31, I127) and a protonation state which is stable in aqueous solution at pH 7.

The phrase "mass number of an oligonucleotide precursor" refers to the sum of the mass numbers of the constituent atoms of the oligonucleotide precursors. The phrase will be denoted by $z(\omega)$.

The phrase "mass number histogram of a mixture of oligonucleotide precursors" $\Omega$ refers to function h from the natural numbers to the natural numbers defined by $h(z)$, where $h(z)$ is the number of oligonucleotide precursors in the mixture $\Omega$ for which $z(\omega)=z$.

The phrase "average ambiguity of a mixture of oligonucleotide precursors" ($A(\Omega)$) refers to the sum of the squares of the values of the mass number histogram of the mixture of oligonucleotide precursors divided by the number of oligonucleotide precursors in the mixture and may be mathematically expressed as:

$$A(\Omega) = 1/N \sum_{Z} h(z)^2$$

The phrase "mass number complexity" (MNC) refers to the number of oligonucleotide precursors in the mixture divided by the average ambiguity of the mixture of oligonucleotide precursors and may be mathematically defined as $$MNC(\Omega) = N/A(\Omega)$$

The phrase "oligonucleotide coverage complexity" $CC_O(\omega)$ may be expressed mathematically as:

$$CC_O(\omega) = 1/4^L \prod_{i=1}^{L} S_{bp}(b_i)$$

where L is the number of nucleotide bases in the oligonucleotide precursor and $b_i$ represents the i'th unit of the oligonucleotide precursor.

The phrase "mixture coverage complexity" ($CC_M(\Omega)$) refers to the sum of the coverage complexities of each of the oligonucleotide precursors in the mixture and may be mathematically expressed as:

$$CC_M(\Omega) = \sum CC_O(\omega)$$

The term "binning" refers to the division of a mixture into defined subset mixtures wherein each individual oligonucleotide of the mixture appears in at least one subset mixture.

The term "composite mixture coverage complexity" refers to the coverage complexity of a set of mixtures that is produced by binning and is equal to the mixture coverage complexity of the original unbinned mixture.

The term "composite mass number complexity" refers to the mass number complexity of a set of mixtures that is produced by binning and is equal to the sum of the mass number complexities of the subset mixtures.

The phrase "direct mass spectral analysis" refers to a method of mass spectral analysis that analyzes either the target nucleic acid sequence itself or the complement of the target nucleic acid sequence. The target nucleic acid sequence itself or its complement may be mass modified, contain additional nucleotide bases or be otherwise modified, provided that the target nucleic acid sequence or its complement is actually mass analyzed. However, the phrase does not include mass spectral analysis wherein a mass tag moiety which is indicative of the presence of target nucleic acid sequence is analyzed, such as those indirect methods described in PCT Application WO 95/04160.

The terms "genericity" or "generic" when applied to a method, refers to a method of mass spectral analysis, which may be applied without reference to certain information. The phrase "positional genericity" refers to methods of mass spectral analysis, which do not require a priori information about the presence, location or identity of mutations in the target nucleic acid sequence. The phrase "target genericity" refers to methods of mass spectral analysis that do not require a priori information about the target nucleic acid.

The term "support" or "surface" refers to a porous or non-porous water insoluble material. The surface can have any one of a number of shapes, such as strip, plate, disk, rod, particle, including bead, and the like. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4methylbutene), polystyrene, polymethacrylate, poly(ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed. Binding of oligonucleotides to a support or surface may be accomplished by well-known techniques, commonly available in the literature. See, for example, A. C. Pease, et al. (*Proc. Nat. Acad. Sci. USA*, 91:5022-5026, 1994).

The term "mutation" refers to variation in nucleotides between two polynucleotides such as in single nucleotide polymorphisms. In general, the variations occur from individual to individual. The mutation may be a change in the sequence of nucleotides of normally conserved nucleic acid sequence resulting in the formation of a mutant as differentiated from the normal (unaltered) or wild-type sequence. Mutations can generally be divided into two general classes, namely, base-pair substitutions and frameshift mutations. The latter entail the insertion or deletion of one to several nucleotide pairs. A difference of a single nucleotide can be significant so to change the phenotype from normality to abnormality as in the case of, for example, sickle cell anemia.

The term "tag" as used herein, generally refers to a chemical moiety which is used to identify a nucleic acid sequence, and preferably but not necessarily to identify a unique nucleic acid sequence. More specifically, "tags" with different molecular weights and therefore distinguishable by mass spectrometry, are used in the present invention to reduce the mass ambiguity between two or more nucleic acid molecules with different nucleotide sequences, but with the identical molecular weights. Preferably, the "tag" is covalently linked to an X-mer precursor through a cleavable linker. Tags of the present invention are analyzable by mass spectrometry. The terms "cleavable mass tags", "releasable tags" are used interchangeably to refer to the tags as defined herein which can be cleaved at the linker to release the tag from the nucleic acid oligonucleotides.

The term "linker" as used herein, is defined as a direct covalent bond or a chemical group, preferably organic, which is used to connect a "tag" molecule to a nucleic acid molecule through one or more covalent bonds. In addition, a "cleavable linker" is one or more direct bonds, or one or more bonds within the linker that is cleavable under conditions which allows the tag to be released from the nucleic acid molecule to which it was attached.

General Comments

The present invention provides methods and reagents to satisfy the need for more sensitive, more accurate and higher throughput analyses of target nucleic acid sequences. The methods and reagents may be generically applied generally to any target nucleic acid sequence and do not require a priori information about the presence, location or identity of mutations in the target nucleic acid sequence.

The reagents of the invention, which are useful for direct mass spectral analysis of nucleic acids and molecular tags linked to nucleic acids, include mixtures comprising natural X-mer precursors, mass-modified X-mer precursors, or natural and mass-modified X-mer precursors where the X-mer precursors have a minimum length of 3 nucleotides. The minimum mixture coverage complexity ($CC_M$) of the mixtures is 56/N, where N is the number of distinct X-mers in the mixture. The length of the X-mer precursors can be selected independently for each X-mer precursor. Each of the X-mer precursors in a mixture is represented by a single chemical species.

The methods and reagents of the present invention reduce the ambiguities present in the mass spectral analysis of a target nucleic acid sequence, and thus, increase the power in all applications utilizing mass spectrometry to analyze the sequence of the target nucleic acid. This reduction is accomplished by employing a mixture of natural and mass-modified oligonucleotide precursors or a mixture of mass-modified oligonucleotide precursors having a high level of mass and coverage complexity. The reduction in ambiguity is also accomplished by employing a mixture of oligonucleotide precursors and a set of tags distinguishable by mass spectrometry, where each tag is covalently linked to at least one oligonucleotide precursor through a cleavable linker.

The reduction in mass ambiguity may be further improved by "binning", i.e., employing subsets of the mixtures in at least two reaction mixtures. The results of the separate interrogation with the subset mixtures could then be combined. In this way, the extent of mass overlap among the released tags for the tagged X-mer reaction products in accordance with the present invention is reduced in a given mass analysis while maintaining a high degree of overall coverage complexity of the target.

The mixtures of the invention are generic or universal in the sense that they may be utilized in any application whose goal is to determine sequence information of a target nucleic acid. Furthermore, the mixtures may be designed without reference to any a priori information about the target nucleic acid sequence, including the presence, location or identity of a mutation, for example. However, this is not meant to imply that the mixtures would not be useful in analyzing target nucleic acid sequences wherein some information was known a priori about the sequence. Nor does it imply that prior information about the target cannot be usefully employed in analysis of the resulting mass spectra.

In general, assays for analyzing nucleic acids coupled with mass analysis do not provide unambiguous information with regard to the sequence. For example, ascertaining the molecular weight of a nucleic acid molecule does not provide the order of nucleotides in the sequence, but rather provides the total weight of the nucleotides of the nucleic acid molecule. Thus, using natural nucleotides, the sequence GGCTTTA is indistinguishable by mass from the sequence CGTTTAG. Therefore, detecting a nucleic acid by mass spectrometry with a mass of 2142 Daltons merely reveals that the oligonucleotide has three Ts, 2 Gs, one A, and one C.

The ambiguity is also increased by the occurrence of fortuitous mass coincidences. In other words, different nucleic acid molecules with different nucleotide compositions have identical masses. For example, oligonucleotides containing either [six As and one T], or [one A, two Cs, three Gs and one T] all have a molecular weight of 2193 Daltons. The general effect of these ambiguities is to shorten the length of the sequence that can be analyzed, since longer sequences result in more mass overlaps (i.e. redundant molecular weights; see FIG. 1).

The ambiguities in molecular weights discussed above can be reduced by altering the mass of the individual oligonucleotide precursors. Methods for using combinations of modified and natural nucleotides in the design of the X-mer precursors are described in the co-pending application U.S. Ser. No. 09/112,437, which result in a greater mass distribution of the X-mer extension and ligation products. For example, the longest nucleic acid target that can be interrogated at a success rate of 95% for a single nucleotide change in the target using the polymerase extension assay and a sequence-complete mixture of the all natural 6-mers (4,096) is about 70 nucleotides. However, this length can be increased by at least a factor of 10 using a carefully designed sequence-complete mixture of 6-mers constructed from the four natural nucleotides (A, G, C and T) and one modified equivalent of each nucleotide, as taught by U.S. Ser. No. 09/112,437. The ambiguity can also be reduced by strategically dividing up the 6-mers into sub-mixtures and running several polymerase extension reactions for each target sequence, where each reaction uses a unique subset of 6-mers.

In one aspect, the present invention provides mixtures comprising X-mer precursors containing mass tags attached through one or more cleavable linkers to reduce or eliminate the mass redundancies for nucleic acid molecules having the same molecular weight but having different sequences. The mass tag is linked to the X-mer precursor via the nucleotide base, ribose ring and/or phosphate backbone through a cleavable covalent bond. Preferably, the linkage of the mass tag to the X-mer precursor does not alter the natural base-pairing properties of the X-mers or interfere with the polymerase extension or ligase reaction.

The cleavage of the linker to release the mass tag from the X-mer may be induced by a variety of methods known in the art. Preferably, cleavage is induced either thermally or through a chemical or photochemical reaction, or through collision induced dissociation. The cleavage reaction is performed as a separate step just prior to the step of mass analysis of the released tag. Alternatively or additionally, the cleavage reaction is performed in the mass spectrometer prior to or during the actual ionization process of the tag.

The use of cleavable mass tags has several advantages. Without limitation to these advantages, since only the mass tag portion of the tagged X-mer is to be analyzed, the absolute mass and resulting mass range needed for the analysis can be kept in the 50 to 1000 mass-to-charge (m/z) range. In addition, the chemical properties of the mass tags can be designed such that they possess a high level of detection sensitivity. These advantages of using cleavable mass tags ease the performance demands of mass spectrometry, and therefore decrease the cost of the analysis. Further, the number of discrete mass tags required to generate a useful sequence-complete mixture of tagged X-mers facilitates the syntheses of the tags. For example, the 4,096 natural 6-mers comprise only 84 discrete masses. Therefore, by tagging all natural 6-mers with tags from a set of 84 tags distinguishable by mass spectrometry after release from the nucleic acids, a mixture comprising all the tagged 6-mers has a reduced level of mass ambiguity.

In addition, the sequences of all natural 6-mers are not evenly distributed among the 84 possible molecular weights but rather have a Gaussian distribution with the peak of the distribution corresponding to sequences having the highest mass redundancy (FIG. 1). For example, there are 6 discrete molecular weights that each have approximately 180 different 6-mer sequences corresponding to that molecular weight. This redundancy increases the overall ambiguity of data from mass spectrometry analyses, and therefore decreases the power of assays using MS.

In contrast, nucleic acid analyses by MS using for example, 6-mers tagged with a similar number of releasable mass tags having discrete molecular weights (84 vs 64-128) is potentially more powerful since the tags can be specifically assigned to a defined X-mer sequence which can allow for a much more even mass distribution rather than a gaussian distribution (FIG. 1). For example, all 4,096 6-mers can be equally distributed among 128 discrete mass tags. Thus a sequence-complete set of 4,096 6-mers specifically tagged with only 128 discrete tags has a mutation identification resolving power greater than the resolving power of an all natural 6-mer mixture.

Reagents of the Invention

Oligonucleotide (X-mer) Precursors

The oligonucleotide precursor (X-mer precursor) reagents of the invention are mixtures of natural X-mer precursors, mass-modified X-mer precursors, or natural and mass-modified X-mer precursors having a minimum length of 3 nucleotides and a mixture coverage complexity of about 15/16 when said mixture contains at least 60 distinct X-mer precursors. The X-mer precursors are each tagged with a chemical moiety through a cleavable linker, where the chemical moiety (tag) is detectable by mass spectrometry. Preferably, the number of tags distinguishable by MS in the mixture is sufficient to (1) reduce the mass ambiguity of the mixture and/or (2) reduce the complexity of the mass spectral analysis by providing moieties for analysis in a range between approximately 50 to 1000 m/z range.

As the average length of the X-mer precursor increases, the number of distinct X-mers in the mixtures of this invention also increases and the mixture coverage complexity may decrease. The lower limit of the mixture coverage complexity is equal to a value of 56 divided by the number of X-mers in the mixture. The length of the X-mer precursors can be selected independently for each X-mer precursor.

The particular composition of the mixture is determined on a case by case basis and will depend upon the demands of the given application. The composition of a mixture is defined by the equations set forth herein. The mixture coverage complexity is defined as:

$$CC_M(\Omega) = \Sigma CC_O(\omega)$$

where $CC_O$ is the oligonucleotide coverage complexity of each of the oligonucleotide precursors in the mixture and is defined as:

$$CC_O(\omega) = 1/4^L \prod_{i=1}^{L} S_{bp}(b_i)$$

where L is the number of nucleotide bases in the oligonucleotide precursor, $S_{bp}$ is base-pairing specificity and $b_i$ represents the i'th unit of the oligonucleotide precursor.

Examples of mixtures having the specifications described above, by way of illustration and not limitation, include; (1) a mixture $\Omega_1$ consisting of 60 of the possible 64 3-mers ($CC_M(\Omega_1)$=15/16, which is greater than 56/60=14/15); (2) a mixture $\Omega_2$ consisting of 128 of the possible 256 4-mers ($CC_M(\Omega_2)$=1/2, which is greater than 56/128=7/16); (3) a mixture $\Omega_3$ consisting of 256 of the possible 1,024 5-mers ($CC_M(\Omega_3)$= 1/4, which is greater than 56/256=7/32); (4) a mixture $\Omega_4$ consisting of 512 of the possible 4,096 6-mers ($CC_M(\Omega_4)$ =1/8, which is greater than 56/512=7/64); (5) a mixture $\Omega_5$ consisting of 1,024 of the possible 4,096 6-mers ($CC_M(\Omega_5)$= 1/4); (6) a mixture $\Omega_6$ consisting of 48 5-mers and 512 6-mers ($CC_M(\Omega_6)$=11/64); (7) a mixture $\Omega_7$ consisting of 128 5-mers, 512 6-mers and 128-7mers ($CC_M(\Omega_7)$=33/128); (8) a mixture $\Omega_8$ consisting of 256 5-mers, 1,000 6-mers and 96 7-mers ($CC_M(\Omega_8)$=1/2).

Examples of mixtures that do not conform to the above specifications, by way of illustration and not limitation include; (1) a mixture $\Omega_9$ consisting of 64 of the possible 256 4-mers (($CC_M(\Omega_9)$=1/4<56/64), (2) a mixture $\Omega_{10}$ consisting of 128 of the possible 1,024 5-mers (($CC_M(\Omega_{10})$=1/8<56/128), (3) a mixture $\Omega_{11}$ consisting of 384 6-mers and 128-7mers (($CC_M(\Omega_{11})$=13/128<56/512), (4) a mixture $\Omega_{12}$ consisting of 64 5-mers, 256 6-mers and 64 7-mers (($CC_M(\Omega_{12})$= 33/256<56/384).

Each X-mer precursor in a mixture or set of submixtures is tagged with a chemical moiety having a mass detectable by mass spectrometry. Tags of the present invention are covalently linked to each X-mer precursor through one or more cleavable linkers. Methods of attaching releasable mass tags to molecules, and nucleic acids in particular, are known in the art (see U.S. Pat. No. 6,027,890). As discussed above, X-mer precursors comprising natural nucleotides have mass redundancies which may be reduced or eliminated by tagging the precursors with molecules having discrete molecular weights.

In one embodiment, the number of discrete tags to be used in a mixture is determined as a percentage of the mass number complexity (MNC) of the mixture without tags and linkers (i.e. before tagging), where each X-mer precursor is extended by one nucleotide (i.e. L+1).

Mass number complexity refers to the number of X-mer precursors in the mixture divided by the average ambiguity of the mixture of X-mer precursors and may be mathematically defined as:

$$MNC(\Omega) = N/A(\Omega)$$

The average ambiguity of the mixture of X-mer precursors ($A(\Omega)$) refers to the sum of the squares of the values of the mass number histogram of the mixture of X-mer precursors divided by the number of X-mer precursors in the mixture and may be mathematically expressed as:

$$A(\Omega) = 1/N \sum_{z} h(z)^2$$

The mass number histogram of a mixture of X-mer precursors (h(z)) refers to function h from the natural numbers to the natural numbers defined by h(z), where h(z) is the number of X-mer precursors in the mixture $\Omega$ for which $z(\omega))=z$.

In the present embodiment, the number of tags in the set of tags covalently linked to X-mer precursors in the mixture is at least 50%, 75%, 90%, 100%, 150%, 200%, 1000% or 10000% of the MNC of the mixture without tags and linkers (i.e. before tagging), where each X-mer precursor is extended by one nucleotide (i.e. L+1), and less than or equal to the number of X-mer precursors in the mixture. As an illustrative example, the number of tags to be used for a mixture is compared to the MNC of the mixture prior to tagging where the mixture comprises all nature 6-mers as X-mer precursors in assays described by the present invention.

The MNC of a mixture of all natural 7-mers is about 53. The 7-mers are the polymerase extension reaction products of all natural 6-mers plus chain-terminating dideoxynucleotides (A description of the methods follow in a subsequent section). The average ambiguity of 7-mers is about 300. Simplistically, the average redundancy in molecular weight of all natural 7-mers is approximately 300. Therefore, since MNC is the number of distinct X-mers (for 7-mers; $4^7$=16384) divided by the average ambiguity (53=16384/300), a useful number of discrete tags is preferably greater than the MNC of the reaction products of untagged X-mer precursors.

For comparison, untagged mass-modified X-mer precursors as described in U.S. Ser. No. 09/112,437, usually the MNC of the mixture is at least about 2 times greater, more usually, at least about 10 times greater, and, most preferably, at least about 50 times greater than the mass number complexity of any natural equivalent of the mixture. For example, the mixture of all natural 4,096 6-mers has a MNC of 53 (see discussion below). A mixture containing all 4,096 6-mers that are synthesized in a combinatorial manner to produce mass-modified X-mers can have an MNC of 348 which is about 6.5 times that of the natural equivalent. Another mixture in which each X-mer is synthesized individually can have an MNC of 559, which is about 10 times that of the natural equivalent. A mixture where each of the 4,096 6-mers possesses a unique mass would have an MNC of 4,096 which is about 77 times that of the natural equivalent.

It is important to recognize that the cleavable mass tag approach disclosed by Southern (WO 95/04160) utilizes a "ladder tag" design where each discrete oligonucleotide sequence within the mixture is associated with a "spectrum" of mass entities. This stands in contrast with tagged X-mer precursors of the present invention where a mixture of tagged X-mers is designed such that any given oligonucleotide sequence in the mixture is attached to preferably a single mass tag with a discrete molecular weight.

In another embodiment, the number of discrete tags (i.e. distinguishable by MS) to be used in a mixture by covalently linking the tags to X-mer precursors is determined as a percentage of the number of X-mer precursors in the mixture. For example, the MNC of a mixture of all natural 7-mers is about 53. The 7-mers are the polymerase extension reaction products of all natural 6-mers plus chain-terminating dideoxynucleotides (A description of the methods follow in a subsequent section). The average ambiguity of 7-mers is about 300. Simplistically, the average redundancy in molecular weight of all natural 7-mers is approximately 300. Therefore, since MNC is the number of distinct X-mers (for 7-mers; $4^7$=16384) divided by the average ambiguity (53=16384/300), a useful number of discrete tags is preferably greater than the MNC of the reaction products of untagged X-mer precursors. Since the MNC of 53 is approximately 1% of the number of all natural 6-mer oligonucleotide precursors (53/4096=1.3%), a preferred number of MS distinguishable tags to use is at least approximately 0.5%, 1%, 2%, 5%, 10%, 20%, 25%, 50%, or 75% of the number of X-mer precursors in a mixture, and less than or equal to the total number of X-mer precursors in the mixture.

In another embodiment, based on the discussion of mass number complexities, a preferred number of tags in a set where a mixture comprises X-mer precursors of 3-mers is greater than 10, 20, 30 or 40; and less than or equal to the number of X-mer precursors in the mixture. For a mixture comprising X-mer precursors of 4-mers, a preferred number of tags in a set of tags covalently linked to the X-mer precursors is greater than 10, 20, 30, 40, 50, 75, 100, 150 or 200; and less than or equal to the number of X-mer precursors in the mixture. For a mixture comprising X-mer precursors of 5-mers, a preferred number of tags in a set of tags covalently linked to the X-mer precursors is greater than 10, 20, 30, 40, 50, 75, 100, 150, 200, 250, 500, 750 or 1000; and less than or equal to the number of X-mer precursors in the mixture. For a mixture comprising X-mer precursors of 6-mers, a preferred number of tags in a set of tags covalently linked to the X-mer precursors is greater than 25, 50, 100, 250, 500, 1000, 2000, 3000 or 4000; and less than or equal to the number of X-mer precursors in the mixture. Based on these examples, those of ordinary skill in the art can determine without undue experimentation the minimum number of MS distinguishable tags to use for a mixture having X-mer precursors with certain nucleotide lengths.

The X-mer precursors useful in the method of the invention have a length of at least 3 nucleotide units. Preferably, the X-mer precursors have a length of at least 4 nucleotide units, more preferably, at least 5 nucleotide units and most preferably at least 6 nucleotide units. The length of the X-mer precursor may be selected independently for each X-mer precursor in the mixture. Thus, it is possible to have a single mixture of X-mer precursors having lengths of 5, 6 and 7 nucleotides. As can be seen from the above discussion, the value, and thus the requirements, for mixture coverage complexity decreases as the length of the X-mer precursor increases. In cases where a single mixture possesses more than one length, the mixture's coverage complexity is obtained by summing the coverage indices of the individual oligonucleotides. Thus, in this case, each oligonucleotide's contribution to the coverage complexity of the mixture would depend on its length: shorter oligonucleotides contribute more. It should be noted that using long oligonucleotides can result in loss in genericity. Lower values of mixture coverage complexity may be used only where loss in genericity can be tolerated. Furthermore, the reagents may comprise a set of mixtures of oligonucleotide precursors. In this case, the mixture coverage complexity (as defined in the Definitions section) of any one member of the set may be lower than that described above, so long as the overall complexity of the mixture conforms to the above description.

The X-mer precursors useful in the method of the invention may each be represented by a single chemical species as opposed to being represented by a number of variants of similar chemical species, such as the ladder of reporter products used to represent the nucleotide sequence in the oligonucleotide described in PCT Application WO 95/04160 (Southern). Thus, each X-mer precursor in the mixture of the invention possess a single mass whereas each oligonucleotide in the mixture of WO 95/04160 is associated with a spectra of masses which represent the nucleotide sequence of interest as discussed above.

To be useful in the methods of the present invention, it is desirable and often necessary to know which X-mer precursors are present in the mixture. However, it is not absolutely necessary to know the level of each X-mer precursor. With this said however, it is advantageous to be able to control the concentration of each X-mer in the mixture to compensate for differences in duplex thermostabilities (see discussion below).

Tags

Molecular tags have been described by U.S. Pat. No. 6,027,890 to Van Ness et al., the teachings of which are incorporated herein by reference in their entirety.

A tag which is useful in the present invention possesses several attributes:

1) A tag is distinguishable from all other tags, preferably by mass spectrometry.

2) The tag is capable of being detected when present at $10^{-22}$ to $10^{-6}$ moles.

3) The tag possesses a chemical handle through which it can be attached to a nucleotide or nucleic acid which the tag is intended to identify, preferably uniquely, but not necessarily. The attachment may be made directly to a nucleic acid, or preferably indirectly through a "linker" group, preferably a cleavable linker.

4) The tag is chemically stable toward all manipulations to which it is subjected, including attachment and cleavage from the nucleic acid molecule, and any manipulations of the nucleic acid molecule while the tag is attached to it.

5) The tag does not significantly interfere with the manipulations performed on the nucleic acid molecule while the tag is attached to it. For instance, if the tag is attached to an oligonucleotide, the tag must not significantly interfere with any hybridization or enzymatic reactions (e.g., PCR sequencing reactions) performed on the oligonucleotide.

To be analyzable by mass spectrometry, the tag should be ionizable. It is thus a preferred element in the design of MS-readable tags to incorporate therein a chemical functionality which can carry a positive or negative charge under conditions of ionization in the MS. This feature confers improved efficiency of ion formation and greater overall sensitivity of detection, particularly in electrospray ionization or atmospheric pressure chemical ionization (EI or APCI). The chemical functionality that supports an ionized charge may be derived from the tag or the linker or both. Factors that can increase the relative sensitivity of an analyte being detected by mass spectrometry are discussed in, e.g., Sunner et al. Anal. Chem. 60:1300-1307 (1988).

A preferred functionality to facilitate the carrying of a negative charge is an organic acid, such as phenolic hydroxyl, carboxylic acid, phosphonate, phosphate, tetrazole, sulfonyl urea, perfluoro alcohol and sulfonic acid. Preferred functionality to facilitate the carrying of a positive charge under ionization conditions are aliphatic or aromatic amines. Examples of amine functional groups which give enhanced detectability of MS tags include quaternary amines (i.e., amines that have four bonds, each to carbon atoms, see Aebersold, U.S. Pat. No. 5,240,859) and tertiary amines (i.e., amines that have three bonds, each to carbon atoms, which includes C=N—C groups such as are present in pyridine, see Hess et al., *Anal. Biochem.* 224:373, 1995; Bures et al., *Anal. Biochem.* 224: 364, 1995). Tertiary amines are particularly preferred. Tertiary and quaternary amines may be alkyl or aryl. A tag-containing moiety must bear at least one ionizable species, but may possess more than one ionizable species. The preferred charge state is a single ionized species per tag. Accordingly, it is preferred that each tag-containing moiety (and each tag variable component) contain only a single amine or organic acid group. Non-limiting examples of suitable amine-containing radicals that may form part of the tag-containing moiety are described by U.S. Pat. No. 6,027,890

The identification of a tag by mass spectrometry is preferably based upon its molecular mass to charge ratio (m/z). The preferred molecular mass range of MS tags is from about 100 to 2,000 daltons, and preferably the tag-containing moiety has a mass of at least about 250 daltons, more preferably at least about 300 daltons, and still more preferably at least about 350 daltons.

As explained above, the tag-containing moiety may contain atoms other than those present in the tag variable component, and indeed other than those present in tag itself. Accordingly, the mass of tag itself may be less than about 250 daltons, so long as the tag-containing moiety has a mass of at least about 250 daltons. Thus, the mass of tag may range from 15 (i.e., a methyl radical) to about 10,000 daltons, and preferably ranges from 100 to about 5,000 daltons, and more preferably ranges from about 200 to about 1,000 daltons.

It is relatively difficult to distinguish tags by mass spectrometry when those tags incorporate atoms that have more than one isotope in significant abundance. Accordingly, preferred tag groups which are intended for mass spectroscopic identification, contain carbon, at least one of hydrogen and fluoride, and optional atoms selected from oxygen, nitrogen, sulfur, phosphorus and iodine. While other atoms may be present in the tag, their presence can render analysis of the mass spectral data somewhat more difficult. Preferably, the tag groups have only carbon, nitrogen and oxygen atoms, in addition to hydrogen and/or fluoride. More preferably, the tags use isotopically pure elements to reduce ambiguity in MS analysis resulting from isotopes. Alternatively or additionally, the isotopic content of each element in the set of tags is known or determined such that contributions to mass peaks from isotopes of elements in MS data can be calculated.

Fluoride is an optional yet preferred atom to have in a tag group. In comparison to hydrogen, fluoride is, of course, much heavier. Thus, the presence of fluoride atoms rather than hydrogen atoms leads to tag groups of higher mass, thereby allowing the tag group to reach and exceed a mass of greater than 250 daltons, which is desirable as explained above. In addition, the replacement of hydrogen with fluoride confers greater volatility on the tag-containing moiety, and greater volatility of the analyte enhances sensitivity when mass spectrometry is being used as the detection method.

The molecular formula of a tag falls within the scope of $C_{1-500}N_{0-100}O_{0-100}S_{0-10}P_{0-10}H_\alpha F_\beta I_\delta$ wherein the sum of $\alpha$, $\beta$, and $\delta$ is sufficient to satisfy the otherwise unsatisfied valencies of the C, N, O, S and P atoms. The designation $C_{1-500}N_{0-100}O_{0-100}S_{0-10}P_{0-10}H_\alpha F_\beta I_\delta$ means that the tag contains at least one, and may contain any number from 1 to 500 carbon atoms, in addition to optionally containing between approximately 0 and 100 nitrogen atoms, between approximately 0 and 100 oxygen atoms, between approximately 0 and 10 sulfur atoms, and between approximately 0 and 10 phosphorus atoms. The symbols $\alpha$, $\beta$, and $\delta$ represent the number of hydrogen, fluoride and iodide atoms in the tag, where any two of these numbers may be zero, and where the sum of these numbers equals the total of the otherwise unsatisfied valencies of the C, N, O, S and P atoms. Preferably, the tag has a molecular formula that falls within the scope of $C_{1-50}N_{0-10}O_{0-10}H_\alpha F_\beta$ where the sum of $\alpha$ and $\beta$ equals the number of hydrogen and fluoride atoms, respectively, present in the moiety.

Linkers

Cleavable linkers for use in accordance with the present invention are known in the art. For example, U.S. Pat. No. 6,027,890 describes the use and synthesis of cleavable linkers for covalent attachment to nucleic acid molecules of interest.

A "linker" component, as used herein, is either a direct covalent bond or an organic chemical group which is used to connect a "tag" to an X-mer precursor or nucleotide through covalent chemical bonds. In addition, the direct bond itself, or one or more bonds within the linker component is cleavable under conditions which allows the tag to be released (i.e. cleaved) from the tag-containing moiety and/or the oligonucleotide. The tag variable component which is present within a tag should be stable to the cleavage conditions.

Preferably, the cleavage can be accomplished rapidly, within a few minutes, and preferably within about 15 seconds or less.

In general, a linker is used to connect each of a large set of tags to each of a similarly large set of oligonucleotides. Typically, a single tag-linker (T-L) combination may be attached to each oligonucleotide of differing sequence. Alternatively or additionally, a single tag-linker combination may be attached to multiple oligonucleotide sequences.

After various manipulations of the set of tagged X-mer precursors and oligonucleotides, special chemical and/or physical conditions are used to cleave one or more covalent bonds in the linker, resulting in the liberation of the tags from the nucleic acids. The cleavable bond(s) may or may not be some of the same bonds that were formed when the tag, linker, and nucleic acids were connected together. The design of the linker will, in large part, determine the conditions under which cleavage may be accomplished. Accordingly, linkers may be identified by the cleavage conditions to which they are particularly susceptible.

Linkers may be photolabile (i.e., prone to cleavage by exposure to actinic radiation). Linkers may also be susceptible to cleavage by acid, base, chemical oxidation, chemical reduction, enzymatic cleavage, electrochemical oxidation or reduction, elevated temperature ("thermal") and thiol exchange.

Certain types of linker are labile to a single type of cleavage condition, whereas others are labile to several types of cleavage conditions. In addition, in linkers which are capable of bonding multiple tags, each of the tag-bonding sites may be labile to different cleavage conditions. For example, in a linker having two tags bonded to it, one of the tags may be labile only to base, and the other labile only to photolysis.

A linker which is useful in the present invention possesses several attributes:

1) The linker possesses a chemical handle through which it can be attached to an oligonucleotide X-mer precursor or a nucleotide precursors.

2) The linker possesses a second, separate chemical handle through which the tag is attached to the linker. If multiple tags are attached to a single linker, then a separate handle exists for each tag.

3) The linker is stable toward all manipulations to which it is subjected, with the exception of the conditions which allow cleavage such that a tag-containing moiety is released from the remainder of the compound. Thus, the linker is stable during attachment of the tag to the linker, attachment of the linker to the nucleic acids, and any manipulations of the nucleic acids while the tag and linker are attached to it.

4) The linker does not significantly interfere with the manipulations performed on the nucleic acids while the T-L is attached to it. For instance, when the T-L is attached to an oligonucleotide, the T-L must not significantly interfere with any hybridization or enzymatic reactions performed on the oligonucleotide in accordance with the teachings of the present invention.

5) Cleavage of the tag from the remainder of the compound occurs in a highly controlled manner, using physical or chemical processes that do not adversely affect the detectability of the tag.

As explained above, a preferred linker has the formula

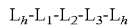

wherein each $L_h$ is a reactive handle that can be used to link the linker to a tag reactant and a nucleotide or oligonucleotide reactant.

$L_2$ is an essential part of the linker, because $L_2$ imparts lability to the linker. $L_1$ and $L_3$ are optional groups which effectively serve to separate $L_2$ from the handles $L_h$.

$L_1$ (which, by definition, is nearer to T than is $L_3$), serves to separate T from the required labile moiety $L_2$. This separation may be useful when the cleavage reaction generates particularly reactive species (e.g., free radicals) which may cause random changes in the structure of the tag-containing moiety. As the cleavage site is further separated from the tag-containing moiety, there is a reduced likelihood that reactive species formed at the cleavage site will disrupt the structure of the tag-containing moiety. Also, as the atoms in $L_1$ will typically be present in the tag-containing moiety, these $L_1$ atoms may impart a desirable quality to the tag-containing moiety.

$L_1$ and/or $L_3$ groups may be a direct bond (in which case the group is effectively not present), a hydrocarbylene group (e.g., alkylene, arylene, cycloalkylene, etc.), —O-hydrocarbylene (e.g., —O—$CH_2$—, O—$CH_2$ $CH(CH_2)$—, etc.) or hydrocarbylene-(O-hydrocarbylene)$_w$—wherein w is an integer ranging from 1 to about 10 (e.g., —$CH_2$—O—Ar—, —$CH_2$—(O—$CH_2CH_2$)$_4$—, etc.).

With the advent of solid phase synthesis, a great body of literature has developed regarding linkers that are labile to specific reaction conditions. In typical solid phase synthesis, a solid support is bonded through a labile linker to a reactive site, and a molecule to be synthesized is generated at the reactive site. When the molecule has been completely synthesized, the solid support-linker-molecule construct is subjected to cleavage conditions which releases the molecule from the solid support. The labile linkers which have been developed for use in this context (or which may be used in this context) may also be readily used as the linker reactant in the present invention.

Lloyd-Williams, P., et al., "Convergent Solid-Phase Peptide Synthesis", Tetrahedron Report No. 347, 49(48): 11065-11133 (1993) provides an extensive discussion of linkers which are labile to actinic radiation (i.e., photolysis), as well as acid, base and other cleavage conditions. Additional sources of information about labile linkers are well known in the art.

As described above, different linker designs will confer cleavability ("lability") under different specific physical or chemical conditions. Examples of conditions which serve to cleave various designs of linker include acid, base, oxidation, reduction, fluoride, thiol exchange, photolysis, and enzymatic conditions.

Examples of cleavable linkers that satisfy the general criteria for linkers listed above will be well known to those in the art and include those found in the catalog available from Pierce (Rockford, Ill.). Examples include:

ethylene glycobis(succinimidylsuccinate) (EGS), an amine reactive cross-linking reagent which is cleavable by hydroxylamine (1M at 37° C. for 3-6 hours);

disuccinimidyl tartarate (DST) and sulfo-DST, which are amine reactive cross-linking reagents, cleavable by 0.015 M sodium periodate;

bis[2-(succinimidyloxycarbonyloxy)ethyl]sulfone (BSO-COES) and sulfo-BSOCOES, which are amine reactive cross-linking reagents, cleavable by base (pH 11.6);

1,4-di-[3'-(2'-pyridyldithio(propionamido)]butane (DP-DPB), a pyridyldithiol crosslinker which is cleavable by thiol exchange or reduction;

N-[4-(p-azidosalicylamido)-butyl]-3'-(2'-pyridydithio) propionamide (APDP), a pyridyldithiol crosslinker which is cleavable by thiol exchange or reduction;

bis-[beta-4-(azidosalicylarnido)ethyl]-disulfide, a photoreactive crosslinker which is cleavable by thiol exchange or reduction;

N-succinimidyl-(4-azidophenyl)-1,3' dithiopropionate (SADP), a photoreactive crosslinker which is cleavable by thiol exchange or reduction;

sulfosuccinimidyl-2-(7-azido-4-methylcoumarin-3-acetamide)ethyl-1,3'-dithio propionate (SAED), a photoreactive crosslinker which is cleavable by thiol exchange or reduction;

sulfosuccinimidyl-2-(m-azido-o-nitrobenzamido)-ethyl-1,3' dithiopropionate (SAND), a photoreactive crosslinker which is cleavable by thiol exchange or reduction.

Other examples of cleavable linkers and the cleavage conditions that can be used to release tags are as follows. A silyl linking group can be cleaved by fluoride or under acidic conditions. A 3-, 4-, 5-, or 6-substituted-2-nitrobenzyloxy or 2-, 3-, 5-, or 6-substituted-4-nitrobenzyloxy linking group can be cleaved by a photon source (photolysis). A 3-, 4-, 5-, or 6-substituted-2-alkoxyphenoxy or 2-, 3-, 5-, or 6-substituted-4-alkoxyphenoxy linking group can be cleaved by $Ce(NH_4)_2(NO_3)_6$ (oxidation). A $NCO_2$ (urethane) linker can be cleaved by hydroxide (base), acid, or $LiAlH_4$ (reduction). A 3-pentenyl, 2-butenyl, or 1-butenyl linking group can be cleaved by $O_3$, $Os_4/IO_4^-$, or $KMnO_4$ (oxidation). A 2-[3-, 4-, or 5-substituted-furyl]oxy linking group can be cleaved by $O_2$, $Br_2$, MeOH, or acid.

Conditions for the cleavage of other labile linking groups include: t-alkyloxy linking groups can be cleaved by acid; methyl(dialkyl)methoxy or 4-substituted-2-alkyl-1,3-dioxlane-2-yl linking groups can be cleaved by $H_3O$; 2-silylethoxy linking groups can be cleaved by fluoride or acid; 2-(X)-ethoxy (where X=keto, ester amide, cyano, $NO_2$, sulfide, sulfoxide, sulfone) linking groups can be cleaved under alkaline conditions; 2-, 3-,4-, 5-, or 6-substituted-benzyloxy linking groups can be cleaved by acid or under reductive conditions; 2-butenyloxy linking groups can be cleaved by $(Ph_3P)_3RhCl(H)$, 3-, 4-, 5-, or 6-substituted-2-bromophenoxy linking groups can be cleaved by Li, Mg, or BuLi; methylthiomethoxy linking groups can be cleaved by $Hg^{2+}$; 2-(X)-ethyloxy (where X=a halogen) linking groups can be cleaved by Zn or Mg; 2-hydroxyethyloxy linking groups can be cleaved by oxidation (e.g., with $Pb(OAc)_4$).

Preferred linkers are those that are cleaved by acid or photolysis. Several of the acid-labile linkers that have been developed for solid phase peptide synthesis are useful for linking tags to oligonucleotides of the present invention. Some of these linkers are described in a recent review by Lloyd-Williams et al. (*Tetrahedron* 49:11065-11133, 1993). One useful type of linker is based upon p-alkoxybenzyl alcohols, of which two, 4-ydroxymethylphenoxyacetic acid and 4-(4-hydroxymethyl-3-methoxyphenoxy)butyric acid, are commercially available from Advanced ChemTech (Louisville, Ky.). Both linkers can be attached to a tag via an ester linkage to the benzylalcohol, and to an amine-containing molecule via an amide linkage to the carboxylic acid. Tags linked by these molecules are released from the oligonucleotides with varying concentrations of trifluoroacetic acid. The cleavage of these linkers results in the liberation of a carboxylic acid on the tag. Acid cleavage of tags attached through related linkers, such as 2,4-dimethoxy-4'-(carboxymethyloxy)-benzhydrylamine (available from Advanced ChemTech in FMOC-protected form), results in liberation of a carboxylic amide on the released tag.

The photolabile linkers useful for this application have also been for the most part developed for solid phase peptide synthesis (see Lloyd-Williams review, supra). These linkers are usually based on 2-nitrobenzylesters or 2-nitrobenzyla- mides. Two examples of photolabile linkers that have recently been reported in the literature are 4-(4-(1-Fmoc-amino) ethyl)-2-methoxy-5-nitrophenoxy)butanoic acid (Holmes and Jones, *J. Org. Chem.* 60:2318-2319, 1995) and 3-(Fmoc-amino)-3-(2-nitrophenyl)propionic acid (Brown et al., *Molecular Diversity* 1:4-12, 1995). Both linkers can be attached via the carboxylic acid to an amine on a nucleic acid. The attachment of the tag to the linker is made by forming an amide between a carboxylic acid on the tag and the amine on the linker. Cleavage of photolabile linkers is usually performed with UV light of 350 nm wavelength at intensities and times known to those in the art. Cleavage of the linkers results in liberation of a primary amide on the tag. Examples of photocleavable linkers include nitrophenyl glycine esters, exo- and endo-2-benzonorbomeyl chlorides and methane sulfonates, and 3-amino-3(2-nitrophenyl) propionic acid. Examples of enzymatic cleavage include esterases which will cleave ester bonds, nucleases which will cleave phosphodiester bonds, proteases which cleave peptide bonds, etc.

Linker handles and methods of attachment are described by U.S. Pat. No. 6,027,890, which is incorporated herein by reference.

A goal of the present invention is to generate either complete mixtures or sets of mixtures having releasable tags analyzable by MS where the tags utilize the available mass range of the mass spectrometer with the concomitant goal of decreasing ambiguity in data from MS analysis of nucleic acids inherent among oligonucleotides having different base-pairing patterns (sequences). In particular, a goal of the present invention is to generate either complete mixtures or sets of mixtures comprising molecular tags attached to oligonucleotides through cleavable bonds, where the tags are analyzable by MS utilize the available mass range of the mass spectrometer with the concomitant goals of reducing the mass ambiguity of oligonucleotides in the mixture or sets of mixtures and identifying sequences of oligonucleotides bonded to the tags. As should be apparent from the discussion herein, the amount and type of information that is sought in a given analysis dictates the type of X-mer mixture required.

X-mer precursors tagged with releasable and MS-analyzable chemical moieties may comprise natural and/or mass-modified nucleotides. There will next be described three methods for synthesizing X-mer precursor mixtures. This is by way of illustration and not limitation. Each of the methods described herein has certain advantages depending upon the degree of synthetic control over the individual oligonucleotides that is required. All three methods utilize standard phosphoramidite chemistries or enzymatic reactions that are known in the art. It is contemplated that different types of mass-modified nucleotide precursor mixtures may be synthesized for defined types of applications. For example, a defined mixture that is easy and inexpensive to manufacture can be used for extremely high throughput, low resolution type assays. More complex mixtures, which may be more expensive to manufacture, can be reserved for higher resolution type applications.

The X-mer precursors may be synthesized by conventional techniques using natural and/or modified nucleotide precursors, including methods employing phosphoramidite chemistry, including both 5'-to-3' and 3'-to-5' synthesis routes. For example, to synthesize all 6-mers requires 4,096 separate synthesis. To facilitate the synthesis of the required number of X-mers, one skilled in the art may also use highly parallel methodologies such as those described in U.S. Pat. No. 5,541, 314 (incorporated herein by reference) and other similar methods. These methods allows for complete synthetic control of each individual X-mer precursor with regard to composition and length.

X-mers may be synthesized, in situ, in either the 3' to 5' or 5' to 3' direction using the 3'-β-cyanoethyl-phosphoramidites or 5'-β-cyanoethyl-phosphoramidites and related chemistries known in the art. In situ synthesis of X-mer precursors may also be performed in the 5' to 3' direction using nucleotide coupling chemistries that utilize 3'-photoremovable protecting groups (U.S. Pat. No. 5,908,926). Alternatively, X-mers may be synthesized on the standard control pore glass (CPG) in the more conventional 3' to 5' direction using the standard 3'-β-cyanoethyl-phosphoramidites and related chemistries (Caruthers M. et al., *Methods Enzymology*, 154; 287-313, 1987; and U.S. Pat. Nos. 4,415,732; 4,458,066) and incorporating a primary amine or thiol functional group onto the 5' terminus of the oligonucleotide (Sproat et al., *Nucleic Acid Res.*, 15;4837, 1987; Connolly and Rider, *Nucleic Acid Res.* 13:4485, 1985).

Individual synthesis also allows for quality control (QC) analysis of each X-mer, which aids in final product manufacturing. Having individual samples of X-mers also allows each X-mer to be assigned and linked to a desired releasable tag. Having individual samples of each X-mer also allows defined subset mixtures to be generated to increase the composite resolution. Moreover, it allows each X-mer to be present in the mixture at a specified concentration. This potentially may be helpful in compensating for different thermostabilities that are expected for each X-mer/target duplex.

The X-mer precursors may be synthesized in parallel or in a single synthesis using standard solid-support phosphoramidite chemistry and a defined series of 25% mixtures of each type of A, C, G and T phosphoramidite. For example, synthesis may be performed stepwise starting from a 25% mixture of each 3'-CPG-linked 5'DMT-protected A, G, C, and T nucleoside. For the synthesis of a mixture of all 4,096 6-mers, five bottles containing a 25% mixture of each A, G, C, and T type of phosphoramidite are prepared for use in each of the five condensation reactions. For example, the bottle for the first condensation step contains a 25% molar equivalent of the phosphoramidites corresponding to; 2'-O-methyl-2,6-diaminopurine, 2'-O-methylguanosine, 2'-deoxy-5-iodocytidine and thymidine. The bottle for the second condensation reaction contains a 25% molar equivalent of the phosphoramidites corresponding to; 2'-deoxyadenosine, 2'-deoxy-7-deazaguanosine, 2'-O-methyl-5(1-propynyl)cytidine and 2'-deoxy-5-fluorouridine. Similar 25% mixture of other types of modified A, G, C and T phosphoramidites are created for the three remaining condensation steps.

In addition, methods of synthesizing tag molecules and covalently attaching them to nucleic acids are known in the art. Preferred methods of synthesis and attachment are described in U.S. Pat. No. 6,027,890, which is incorporated herein by reference. Briefly, a preferred method of synthesizing tags utilizes combinatorial chemistry. Combinatorial chemistry is a type of synthetic strategy which leads to the production of large chemical libraries (see, for example, PCT Application Publication No. WO 94/08051). These combinatorial libraries can be used as tags for the identification of nucleic acid sequences and molecules in accordance with the present invention. Combinatorial chemistry may be defined as the systematic and repetitive, covalent connection of a set of different "building blocks" of varying structures to each other to yield a large array of diverse molecular entities. Building blocks can take many forms, both naturally occurring and synthetic, such as nucleophiles, electrophiles, dienes, alkylating or acylating agents, diamines, nucleotides, amino acids, sugars, lipids, organic monomers, synthons, and combinations of the above. Chemical reactions used to connect the building blocks may involve alkylation, acylation, oxidation, reduction, hydrolysis, substitution, elimination, addition, cyclization, condensation, and the like. This process can produce libraries of compounds which are oligomeric, non-oligomeric, or combinations thereof. If oligomeric, the compounds can be branched, unbranched, or cyclic. Examples of oligomeric structures which can be prepared by combinatorial methods include oligopeptides, oligonucleotides, oligosaccharides, polylipids, polyesters, polyamides, polyurethanes, polyureas, polyethers, poly(phosphorus derivatives), e.g., phosphates, phosphonates, phosphoramides, phosphonamides, phosphites, phosphinamides, etc., and poly(sulfur derivatives), e.g., sulfones, sulfonates, sulfites, sulfonamides, sulfenamides, etc.

One common type of oligomeric combinatorial library is the peptide combinatorial library. Recent innovations in peptide chemistry and molecular biology have enabled libraries consisting of tens to hundreds of millions of different peptide sequences to be prepared and used. Such libraries can be divided into three broad categories. One category of libraries involves the chemical synthesis of soluble non-support-bound peptide libraries (e.g., Houghten et al., *Nature* 354:84, 1991). A second category involves the chemical synthesis of support-bound peptide libraries, presented on solid supports such as plastic pins, resin beads, or cotton (Geysen et al., *Mol. Immunol.* 23:709, 1986; Lam et al., *Nature* 354:82, 1991; Eichler and Houghten, *Biochemistry* 32:11035, 1993). In these first two categories, the building blocks are typically L-amino acids, D-amino acids, unnatural amino acids, or some mixture or combination thereof. A third category uses molecular biology approaches to prepare peptides or proteins on the surface of filamentous phage particles or plasmids (Scott and Craig, *Curr. Opinion Biotech.* 5:40, 1994). Soluble, nonsupport-bound peptide libraries appear to be suitable for a number of applications, including use as tags.

The available repertoire of chemical diversities in peptide libraries can be expanded by steps such as permethylation (Ostresh et al., *Proc. Natl. Acad. Sci., USA* 91:11138, 1994). Numerous variants of peptide combinatorial libraries are possible in which the peptide backbone is modified, and/or the amide bonds have been replaced by mimetic groups. Amide mimetic groups which may be used include ureas, urethanes, and carbonylmethylene groups. Restructuring the backbone such that sidechains emanate from the amide nitrogens of each amino acid, rather than the alpha-carbons, gives libraries of compounds known as peptoids (Simon et al., *Proc. Natl. Acad. Sci., USA* 89:9367, 1992).

Another common type of oligomeric combinatorial library is the oligonucleotide combinatorial library, where the building blocks are some form of naturally occurring or unnatural nucleotide or polysaccharide derivatives, including where various organic and inorganic groups may substitute for the phosphate linkage, and nitrogen or sulfur may substitute for oxygen in an ether linkage (Schneider et al., *Biochem.* 34:9599, 1995; Freier et al., *J. Med. Chem.* 38:344, 1995; Frank, J. *Biotechnology* 41:259, 1995; Schneider et al., Published PCT WO 942052; Ecker et al., *Nucleic Acids Res.* 21:1853, 1993).

More recently, the combinatorial production of collections of non-oligomeric, small molecule compounds has been described (DeWitt et al., *Proc. Natl. Acad. Sci., USA* 90:690, 1993; Bunin et al., *Proc. Natl. Acad. Sci., USA* 91:4708, 1994). Structures suitable for elaboration into small-molecule libraries encompass a wide variety of organic molecules, for example heterocyclics, aromatics, alicyclics, aliphatics, steroids, antibiotics, enzyme inhibitors, ligands, hormones, drugs, alkaloids, opioids, terpenes, porphyrins, toxins, catalysts, as well as combinations thereof.

In another embodiment of methods for synthesizing tags, two methods for the preparation and use of a diverse set of amine-containing MS tags are described in U.S. Pat. No. 6,027,890, details and teachings of which are incorporated herein by reference. Briefly, in both methods, solid phase synthesis is employed to enable simultaneous parallel synthesis of a large number of tagged linkers, using the techniques of combinatorial chemistry. In the first method, the eventual cleavage of the tag from the oligonucleotide results in liberation of a carboxyl amide. In the second method, cleavage of the tag produces a carboxylic acid.

Effects of X-mer Modifications on Mass Spectroscopic, Thermodynamic, and Enzymatic Properties The composition of the X-mer precursors directly influences the overall specificity and sensitivity of the assay. Moreover, having control over both their design and mode of synthesis allows for the incorporation of modifications that aid in their use in the methods of the invention. Suitable modifications include incorporating non-bridging thiophosphate backbones, 5'-N-phosphoamidite internucleotide linkages and the like.

The modification may increase the thermodynamic stability of the hybrids formed between the X-mer precursor and target nucleic acid sequence analyte to normalize the thermodynamic stability of the hybrids within the mixture. For example, 2,6-diaminopurine forms more stable base-pairs with thymidine than does adenosine. In addition, incorporating 2'-fluoro-thymidine increase the stability of A-T base pairs whereas incorporating 5-bromo and 5-methyl cytidine increases the stability of G-C base pairs.

In addition, use of universal bases may be used to increase thermodynamic stability of the hybrids without altering complementary hybridization properties of the X-mer precursors. For example, the universal nucleotide 5-nitroindole may be added to the 5'-ends of X-mer precursors. It has been shown that adding three or four 5-nitroindole bases on their 5' termini of 8-mers can significantly improve their ability to prime sequencing reactions (Ball et al. *Nucleic Acids Research* 26:5225-5227, 1998). Without limitation to theory, it was proposed that the improvement in priming sequencing reactions is due to an increase in non-specific base stacking between the target and the 5-nitroindole bases. The universal nucleotides added increase the difference in the intrinsic thermodynamic stability between perfect and single mismatch duplexes which could aid in discriminating between the more poorly recognized terminal mismatches (Fotin et al. *Nucleic Acids Research* 26:1515-1521, 1998).

Alternatively or additionally, universal nucleotides (e.g. 5-nitroindole nucleotide) may be incorporated at internal positions within the X-mers. Internal incorporation will allow the increase in the effective length of the X-mers without having to increase the total number of X-mers within the reaction mixture needed to maintain a sequence-complete mixture. For example, the four related 7-mer sequences AAGACTG, AAGGCTG, AAGTCTG, and AAGCCTG could be represented by a single 7-mer AAGZCTG (where Z is the universal nucleotide 5-nitroindole). A 7-mer mixture based on the architecture NNNZNNN (N equals A, C, G or T) has the same resolving power as that of a 6-mer mixture. Likewise, an 8-mer mixture having the architecture NNZN-NZNN also has the same power as that of the 6-mer mixture. Thus, by increasing the X-mer length using universal bases, both the thermodynamic stability and kinetic advantage of the X-mer/target duplex may be increased without the need to increase the overall number of X-mers in the reaction mixture.

In another embodiment, hybrid stability between X-mer precursors and target sequences may be increased using minor groove binding molecules (MGB) attached to X-mer precursors. Use of MGB therefore, increases the duplex hybrid stability without altering the sequence information content of the X-mer precursors and mixtures comprising X-mer precursors (see Kutyavin et al. *Nucleic Acids Research* 25: 3718-3723, 1997 incorporated herein by reference). For example, Kutyavin et al. (supra) used a tethered dihydropyrroloindole tripeptide to increase nucleic acid duplex stability in duplexes comprising the tripeptide by as much as 40-49 degrees C.

The mass modification may decrease the thermodynamic stability of the hybrids formed between the X-mer precursor and target nucleic acid sequence analyte to normalize the thermodynamic stability of the hybrids within the mixture. A-T base pairs can be destabilized by incorporating 2'-aminonucleosides. Inosine can also be used in place to guanosine to destabilized G-C base pairs. Incorporating N-4-ethyl-2'-deoxycytidine has been shown to decrease the stability of G-C base pairs. Incorporating the latter can normalize the stability of any given duplex sequence to an extent where its stability is made independent of A-T and G-C content (Nguyen et al., *Nucleic Acids Res.* 25, 3095 (1997)).

Modifications that reduce fragmentation of the oligonucleotide due to the ionization processes in mass spectrometry can also be introduced. For example, one approach is a 7-deaza modification of purines to stabilize the N-glycosidic bond and hence reduce fragmentation of oligonucleotides during the ionization process (see, for example, Schneider and Chait, *Nucleic Acids Res* 23:1570 (1995)). Modification of the 2' position of the ribose ring with an electron withdrawing group such as hydroxyl or fluoro may be employed to reduce fragmentation by stabilizing the N-glycosidic bond (see, for example, Tang, et al., *J Am Soc Mass Spectrom*, 8, 218-224, 1997).

Mass-tagged Chain-terminating Nucleotides

The use of chain-terminating nucleoside triphosphates such as dideoxynucleoside triphosphates in the present invention for the method of PEA is fundamentally different from that known in the art. Methods of the present invention utilize chain-terminating nucleotides as a means of "scoring" (or capturing) hybridization events between the target nucleic acid and a multitude of tagged X-mer precursors by shifting the mass of the resulting extension products out of the mass range of the unextended X-mer precursors. For untagged X-mer precursors, this specific function dictates that the X-mer precursors that have hybridized to target nucleic acids be separable from non-hybridizing X-mer precursors.

In other words, the reaction of polymerase extension is to mark X-mer precursors hybridizing to complementary target nucleic acids. Such hybridization is inherently transient due to non-covalent hydrogen-bonding interactions. Therefore, by adding one or more nucleotides, preferably including a chain-terminating nucleotide, through the polymerase extension reaction, those X-mer precursors which have hybridized to target sequences can be separated from non-hybridizing X-mer precursors, thus providing sequence information on the target.

For example when separating X-mer PEA reactions products from precursors by mass, the mass range for an X-mer precursor mixture composed all 6-mers generated from the four natural deoxynucleotides will range from 1,667 atomic mass units (amu) for ($C_6$) to 1,907 amu for ($G_6$). This gives a mass range difference of 240 amu. The masses of the individual natural dideoxynucleotides (the monophosphate form minus the mass of a water molecule) are 296, 312, 272, and 287 amu for pddA, pddG, pddC, pddT respectively. Thus because the absolute mass of each dideoxynucleotide is greater than the mass range for the natural 6-mer mixture, they are sufficient for partitioning the masses of the X-mer precursors and X+1-mer extension products. If, however, the mass range of the X-mer precursors is increased, for example, by the introduction of mass-modifications or by employing X-mers of mixed lengths, then it is desirable to mass-tag the chain-terminating nucleotide so that the masses of all extension products are greater than that of all X-mer precursors. This would aid in the separation of the tagged X-mer reaction products from the unreacted tagged X-mer precursors when employing mass spectrometry separation methods.

Methods of the Invention

Generating Short Word Content Representations of Target Nucleic Acids

Figure 2B:
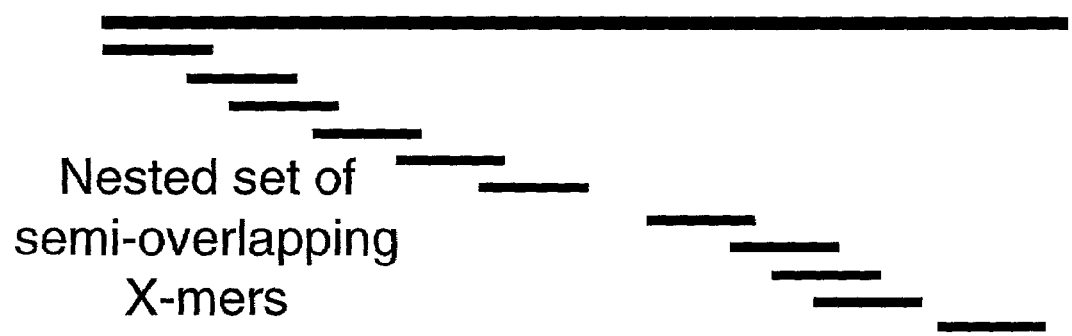
Figure 2C:
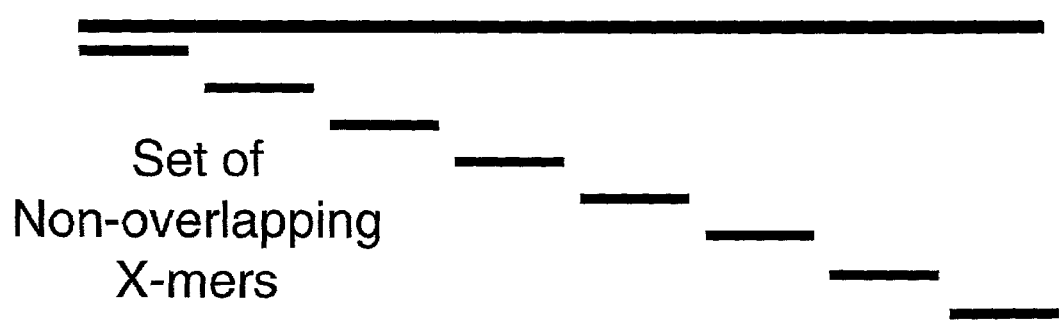

The invention is directed to methods and reagents for recapitulating a target nucleic acid in the form of a set of oligonucleotides (X-mers) that are complementary to the target sequence, and analyzing the set molecular tags released from the X-mers complementary to the target sequence by mass spectroscopy. The set of oligonucleotides represents the "short word" content of the target, which gives defined sequence information about the target. The set of oligonucleotides that represent a target can be of three general types (FIG. 2). The nested set of overlapping X-mers (FIG. 2a) is characterized by having extensive overlap among the X-mers in the set. The nested set of semi-overlapping X-mers (FIG. 2b) has less overlap among the X-mers whereas the non-overlapping set of X-mers (FIG. 2c) has no overlap. For all three types of sets, the X-mer length within a given set need not be constant. In general, the X-mers in the nested set of overlapping X-mers have a length of about 3 to about 18, usually about 5 to about 14, nucleotides. For this set, the overlap is all but one nucleotide along the entire length of the target nucleic acid sequence. In general, the X-mers in the nested set of semi-overlapping X-mers have a length of about 3 to about 18, usually about 5 to about 14, nucleotides. In general, the X-mers in the nested set of non-overlapping X-mers have a length of about 3 to about 18, usually about 4 to about 14, nucleotides. For all three approaches the X-mers sample the entire length of the target nucleotide sequence. The actual number of X-mers generated is generally determined by the length of the target nucleotide sequence and the desired result. The number of X-mers should be sufficient to achieve the goals of the defined application. For example, if the goal is to perform mutation detection, then a sufficient number of X-mers are needed in order to distinguish the X-mer or set of X-mers that encompass the mutation.

General Description of the Methods

One aspect of the present invention is a method of analyzing a target nucleic acid sequence. A mixture of X-mer precursors is hybridized to the target nucleic acid sequences. The mixture comprises natural X-mer precursors, mass-modified X-mer precursors, or natural and mass-modified X-mer precursors having a minimum length of 3 nucleotides. X-mer precursors of the present invention also have tags analyzable by MS which are covalently linked to the X-mer precursors through cleavable linkers.

The mixture has a mixture coverage complexity about 15/16 when said mixture contains at least 60 distinct X-mer precursors for a mixture of 3-mers for example. As the average length of the X-mer precursor increases, the number of distinct X-mers in the mixtures of this invention also increases and the mixture coverage complexity may decrease. The lower limit of mixture coverage complexity for a mixture (or a composite mixture coverage complexity for a sub-mixture) is equal to 56/N, where N is the number of X-mers in the mixture. The length of the X-mer precursors can be selected independently for each X-mer precursor.

In one embodiment, the hybrids are processed to mark the X-mer precursor portions of the hybrids that have hybridized to complementary sequences in a target sequence-mediated reaction, such that X-mer precursors that have hybridized to target sequence can be separated from non-hybridizing X-mer precursors. It is preferred that X-mer precursors that have hybridized to a complementary target sequence are processed to differentiate the hybridizing (i.e. complementary) X-mers from the non-hybridizing (i.e. non-complementary) X-mer precursors. The processed X-mer precursors are separated from the non-processed precursors. Linkers of the processed X-mer precursors are cleaved to release the MS-analyzable tags. Mass analysis of the tags will provide sequence information to the X-mer precursors that have hybridized to complementary target sequences. The steps of method may be carried out in solution or with surface-bound nucleic acids such as in an array. Solution-based systems may be preferred because they are governed by standard solution mass-action and diffusion processes.

Preparation of the X-mer Mixture:

The first step of the method of the invention is preparing a mixture of X-mer precursors having an appropriate coverage complexity for the given application and an appropriate set of MS-analyzable tags assigned to X-mer precursors of known sequence such that data from MS analysis of released tags provides sequence information on X-mer precursors which have hybridized to complementary target nucleic acid sequences. The X-mer precursor mixture may also possess the attributes described herein regarding ionization and thermodynamic properties. The design and preparation of the X-mer precursor mixture may be carried out as described herein.

Processing Step

After hybridizing X-mer precursors to target nucleic acids, the second step of the method of the invention is processing the hybrids to mark the X-mer precursor portions of the hybrids as described herein. The alteration may be accomplished either by an enzymatic or chemical reaction. Suitable enzymatic techniques include a polymerase extension assay, a ligase assay and the like. Suitable chemical techniques include condensation of activated X-mer precursors using carbodiimides and cyanogen bromide derivatives and the like. Marking X-mer precursors may also be accomplished by directly or indirectly (i.e. biotinylation and binding to streptavidin; and/or digoxigenin) incorporating a signal-producing chemical moiety, such as a fluorescent or radioactive marker. The following discussion is a brief description of some of the various processes; a more detailed discussion is set forth below.

Polymerase Extension Assay

For the Polymerase Extension Assay (PEA), the hybridized X-mer precursors are extended by polymerizing a single nucleotide at the 3'-end of the hybridized X-mer precursors using a nucleotide polymerase (see FIG. 3).

Ligase Assay

Figure 4:
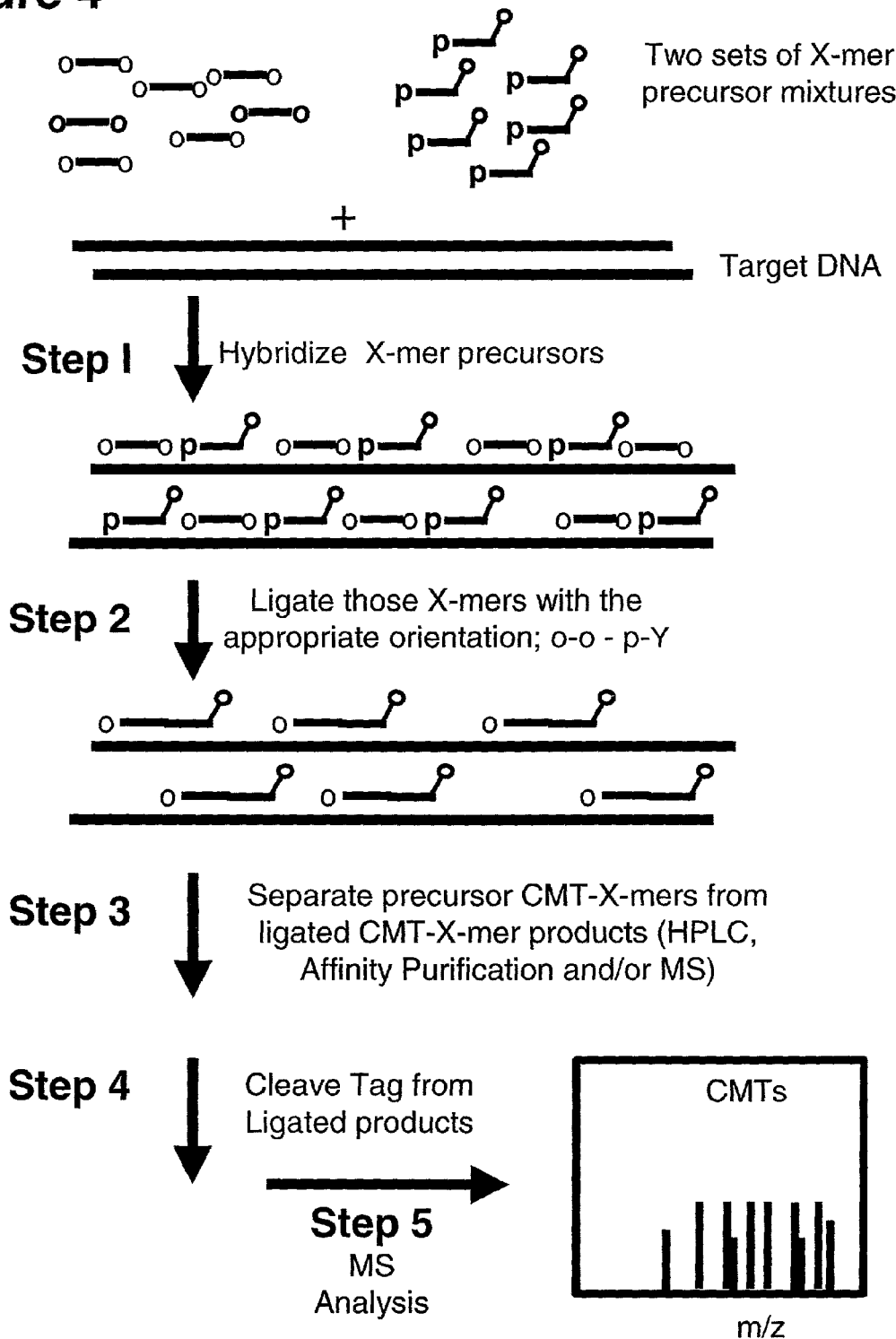
FIG. 4 is a diagram outlining the steps of the X-mer Ligation Assay (XLA) using cleavable mass tags (CMT-XLA).

For the X-mer Ligation Assay (XLA), adjacent hybridized X-mer precursors are ligated together prior to analysis using a ligase (see FIG. 4). It is preferred that the X-mer precursors be of a length sufficient to serve as good substrates for ligation by the ligase yet not too long to serve as templates for ligation of complementary X-mer precursors within the reaction mixture. It should be noted that, although it is preferable that all of the adjacent hybridized X-mer precursors are ligated, it is not a requirement.

For XLA, ligation of an X-mer precursor to an adjacent X-mer precursor marks those X-mer precursors that have hybridized to a target sequence. Thus separation of ligated X-mer precursors from unligated X-mer precursors and determining the sequences of the ligated products provides nucleotide sequence data for target nucleic acids.

In one embodiment, X-mer precursors with 5' phosphate ends and blocked 3' ends (e.g. non 3'-OH and/or non 3' phosphorylated ends; chemical blocking groups; or tags attached at 3' ends) are tagged with releasable tags in accordance with the present invention. In addition, non-tagged X-mer precursors having 5'-OH (or blocked 5' ends) and 3'-OH ends such that ligation between tagged and non-tagged X-mer precursors occurs with one orientation. Ligated products may be separated from non-ligated X-mer precursors in accordance with a physical property such as mass, affinity, energy emission (e.g. light, fluorescence, radioactivity) using well known techniques such as MS, chromatography (e.g. HPLC), and fluorescence activated sorting.

The method of XLA in accordance with the present invention includes the steps of (as described in FIG. 4):

1) hybridizing X-mer precursors in a mixture or sub-mixture to a target nucleic acid;
2) ligating hybridizing X-mer precursors with the proper chemical composition and orientation of 3' and 5' ends;
3) separating ligated X-mer precursors from unligated X-mer precursors;
4) releasing tags from separated ligated X-mer precursors by cleaving linkers;
5) analyzing tags by MS to provide sequence information on the target sequence.

Figure 5:
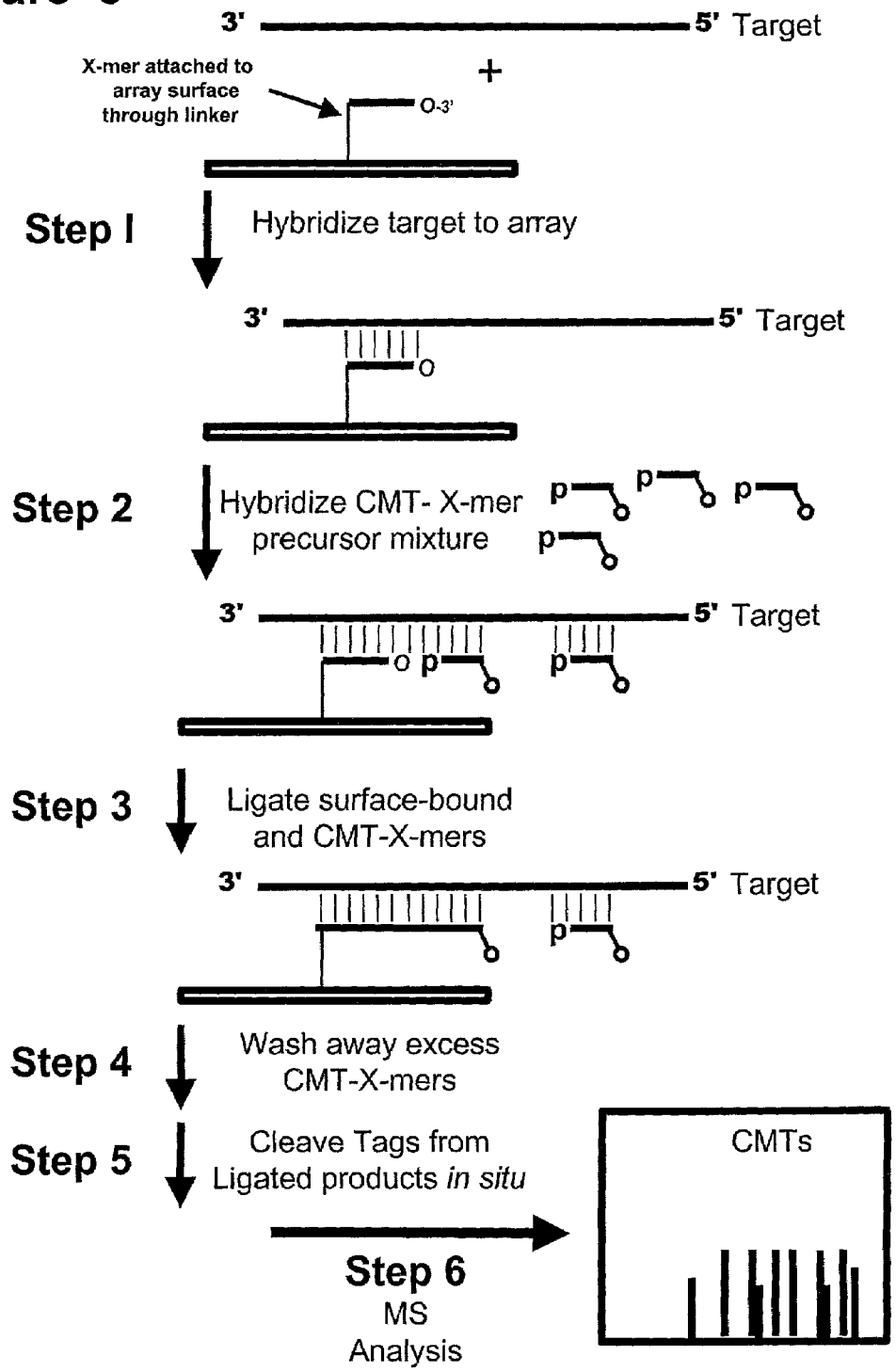
FIG. 5 is a diagram outlining the steps of the Array-based X-mer Ligation Assay using cleavable mass tags (CMT-AXLA).

The ligation assay may be conducted with surface-bound arrays (see FIG. 5). The arrays have a surface and a multiplicity oligonucleotide probes attached thereto. The probes contain a linker attached to the surface and a nucleic acid sequence having a 5'-end attached to the linker and a terminal 3'-OH.

The method includes the following steps:
(1) hybridizing the target nucleic acid sequence to the probes;
(2) adding the mixture of tagged X-mer precursors to the target nucleic acid sequence;
(3) ligating the hybridized X-mer precursors located adjacent to the terminal 3'-OH ends of the surface-bound probe to form a hybridized precursor/probe complex with the target nucleic acid sequence attached thereto;
(4) removing non-ligated tagged X-mer precursors;
(5) releasing tags from ligated X-mer precursors by cleaving linkers attaching tags to X-mer precursors; and
(6) analyzing the set of released tags via mass spectrometry to provide sequence information on the target sequence.

Detailed Description of the Methods

The following description is directed to general methods for generating oligonucleotide sets that represent the short-word content of the target. Each method can generate one or more types of oligonucleotide sets depending upon the reagents used. This description is by way of illustration and not limitation. As mentioned above, one method is termed "Polymerase Extension Assay" (PEA). Another method is termed the "X-mer Ligation Assay" (XLA).

Fundamental to all methods are oligonucleotide (X-mer) mixtures composed of natural and/or mass-modified nucleotides that contain releasable MS-analyzable tags attached to the X-mers through cleavable linkers. It should be understood that different sets of mixtures can be designed to generate the different types of sets and thus provide various amounts of target sequence information. By analysis of the mass peaks present in the mass spectra generated in the above methods, and correlation of these peaks with information about the tags linked to the X-mer precursors in the mixture responsible for each mass spectrum, and possibly a priori information about the target sequence, the information sought from the target is determined.

PEA is a generic method for generating nested sets of overlapping and semi-overlapping X-mers. The steps of the PEA method are depicted in FIG. 3. In Step 1, a mixture (or set of mixtures) of X-mers representing either all possible X-mer sequences or subsets thereof are allowed to hybridize at random positions along the target nucleic acid sequence according to Watson-Crick base-pairing rules. In Step 2, the hybridized X-mers are extended by a single nucleotide using a nucleotide polymerase such as a DNA- or RNA-dependent DNA polymerase and a mixture of one or more chain-terminating nucleoside triphosphates such as dideoxynucleotide-triphosphates. In Step 3, the resulting extended X-mers, i.e., X+1-mer extension products, are separated from non-extended X-mers. In step 4, tags from the separated and extended X-mer precursors (i.e. reaction products) are released by cleavage of the linkers. In step 5, the set of released tags is analyzed by mass spectroscopy to provide sequence data on the target nucleic acid(s).

The extent of overlap among the X+1-mer products depends upon the sequence completeness of the interrogating X-mer mixture. For example, if all 4,096 6-mers and all four ddNTP's are present in the interrogating mixture, then the maximal overlap among the resulting 7-mer products is possible. Providing a subset of the 4,096 possible 6-mers and/or a subset of the four ddNTP's results in less overlap among the 7-mer products and potential gaps in the sequence coverage. Alternatively or additionally, PEA as used in accordance with the present invention may be performed with a subset of the 4 ddNTP or preferably with one of the four ddNTPs. Thus PEA reaction products when analyzed by MS according to the present invention contain additional sequence information because the identity of the extended nucleotide is known.

If the extended products are separated by mass from the non-extended X-mer precursors, it is then preferred that the chain-terminating nucleotides have sufficient mass to effectively partition the X-mer precursor mixture and X+1-mer extension products. It should be noted that, while it is preferable that all of the hybridized X-mer precursors are extended, it is not a requirement. In the present invention the greater the number of hybridized X-mer precursors extended, the more accurate the determination.

The combination of reagents is subjected to conditions under which the X-mers hybridize to the target nucleic acid and are extended by one nucleotide in the presence of a chain-terminating nucleoside triphosphate that is complementary to nucleotide of the target adjacent to the hybridized X-mer. Generally, an aqueous medium is employed. Other polar cosolvents may also be employed, usually oxygenated organic solvents of from 1-6, more usually from 1-4, carbon atoms, including alcohols, ethers and the like. Usually these co-solvents, if used, are present in less than about 70 weight percent, more usually in less than about 30 weight percent.

The pH for the medium is usually in the range of about 4.5 to 9.5, more usually in the range of about 5.5 to 8.5, and preferably in the range of about 6 to 8. Various buffers may be used to achieve the desired pH and maintain the pH during the determination. Illustrative buffers include borate, phosphate, carbonate, Tris, HEPES, barbital and the like. The particular buffer employed is not critical to this invention but in individual methods one buffer may be preferred over another.

The reaction is conducted for a time sufficient to produce the extended X+1-mers, which contain a chain terminating nucleoside triphosphate. Generally, the time period for conducting the entire method will be from about 10 to 200 minutes. It is usually desirable to minimize the time period.

The concentration of the nucleotide polymerase is usually determined empirically. Preferably, a concentration is used that is sufficient to extend most if not all of the precursor X-mers that specifically hybridize to the target nucleic acid (see below). The primary limiting factors are generally reaction time and cost of the reagent.

The number of the target nucleic acid molecules can be as low as $10^6$ in a sample but generally may vary from about $10^6$ to $10^{13}$, more usually from about $10^8$ to $10^{12}$ molecules in a sample, preferably at least $10^{-13}$ M in the sample and may be $10^{-13}$ to $10^{-6}$ M, more usually $10^{-11}$ to $10^{-7}$M. In general, the reagents for the reaction are provided in amounts to achieve extension of the hybridized X-mers. The number of each X-mer precursor molecules is generally $10^{10}$ and is usually about $10^{10}$ to about $10^{13}$, preferably, about $10^{11}$ to about $10^{12}$ for a sample size that is about 10 microliters. The concentration of each X-mer precursor may be adjusted according to its thermostability as discussed above. The absolute ratio of target to X-mer precursor is to be determined empirically. The concentration of the chain-terminating nucleoside triphosphates in the medium can vary depending upon the affinity of the nucleoside triphosphates for the polymerase. Preferably, these reagents are present in an excess amount. The nucleoside triphosphates are usually present in about $10^{-7}$ to about $10^{-4}$ M, preferably, about $10^{-6}$ to about $10^{-5}$ M.

The reaction temperature can be in the range of from about 0° C. to about 95° C. depending upon the type of polymerase used, the concentrations of target and X-mers and the thermodynamic properties of the X-mers in the mixture. For example, at 40 nM target nucleic acid sequence, 40 nM 6-mer, and 7 nM Bst Polymerase, between 20% and 50% of the 6-mer can be extended at 5° C. in 2 hours depending upon the sequence of the 6-mer. Similar extension efficiencies are obtained at 20° C. indicating that the extension efficiency is not solely dependent upon the thermodynamics of the X-mer/target interaction. Importantly, it may be beneficial to cycle the incubation temperature. Cycling could help to expose structured region of the target for X-mer binding and subsequent extension as well as facilitate turnover of the extension products. Thus, the overall sensitivity of PEA could be markedly increased by allowing a given target molecule to act as a template for multiple X-mer binding and subsequent extension reactions. In accordance with this aspect of the invention, one cycle may be carried out at a temperature of about 75° C. to about 95° C. for about 0.1 to 5 minutes, more usually about 0.5 to 2 minutes and another cycle may be carried out at a temperature of about 5° C. to about 45° C. for about 1 to 20 minutes, more usually about 5 to 15 minutes. The number of cycles may be from about 2 to about 20 or more. In general, the cycle temperatures and duration are selected to provide optimization of the extension of the hybridized X-mer of given length.

The order of combining of the various reagents to form the combination may vary. Usually, the sample containing the target polynucleotide is combined with a pre-prepared combination of chain-terminating nucleoside triphosphates and nucleotide polymerase. The X-mers may be included in the prepared combination or may be added subsequently. However, simultaneous addition of all of the above, as well as other stepwise or sequential orders of addition, may be employed provided that all of the reagents described above are combined prior to the start of the reactions.

XLA is another generic method for generating nested sets of overlapping and semi-overlapping X-mers. The basic steps for this method are depicted in FIG. 4. In step 1, mixtures of X-mers representing either all possible X-mer sequences or subsets thereof are allowed to hybridize at random positions along the target nucleic acid sequence according to Watson-Crick base-pairing rules. One mixture has oligonucleotides having 3'-OH ends and 5'-OH (or 5' blocked) ends. Preferably but not necessarily, oligonucleotides of this mixture are not tagged. A second mixture comprises X-mer precursors tagged with releasable tags and further comprising 5'-phosphate groups and blocked 3' ends to prevent ligation at the 3' end. In step 2, the X-mers that hybridize adjacent to one another in the proper orientation are ligated together enzymatically using a ligase such as DNA ligase that assists in the formation of a phosphodiester bond to link two adjacent bases in separate oligonucleotides. Such ligases include, for example, T4 DNA ligase, Taq DNA Ligase, *E. coli* DNA Ligase and the like. Alternatively, adjacent X-mer precursors may be ligated chemically using a condensing agent. Suitable condensing agents include, for example, carbodiimides, cyanogen bromide derivatives, and the like. In step 3, the resulting ligated X-mer products are separated from unligated X-mers. In step 4, the tags from the ligated X-mers having tags are released by cleavage of the cleavable linkers. In step 5, the set of tags released is analyzed by mass spectroscopy to provide information on the sequence of the target nucleic acids.

The conditions for carrying out the reactions in this approach are similar to those described above. The pH for the medium is usually in the range of about 4.5 to 9.5, more usually in the range of about 5.5 to 8.5, and preferably in the range of about 6 to 8.

The reaction is conducted for a time sufficient to produce the desired ligated product. Generally, the time period for conducting the entire method will be from about 10 to 200 minutes. It is usually desirable to minimize the time period.

The reaction temperature can vary from 0° C. to 95° C. depending upon the type of ligase used, the concentrations of target and X-mers and the thermodynamic properties of the X-mers in the mixture. As in the case of PEA, it may be beneficial to cycle the incubation temperature to help expose structured region of the target for X-mer binding and subsequent ligation as well as to facilitate turnover of the ligated products.

The concentration of the ligase is usually determined empirically. Preferably, a concentration is used that is sufficient to ligate most if not all of the precursor X-mers that specifically hybridize to the target nucleic acid. The primary limiting factors are generally reaction time and cost of the reagent.

The concentration of each X-mer precursor is generally as described above for PEA and may be adjusted according to its thermostability as discussed above. The absolute ratio of target to X-mer precursor is to be determined empirically.

The level of phosphorylation of the 5' terminus of the X-mer mixture can affect the extent of ligation (overall number of ligated products) and the length of ligation products (value of n). The extent and length of ligation can also be controlled by introducing a modification at the 3' terminus of the X-mer mixture that blocks ligation. In one approach two sets of X-mer mixtures are used together in a single ligation reaction mixture. The X-mers in the first X-mer mixture possess a 5' phosphorylated terminus and a 3' blocked terminus (5'p-y3') where the X-mers are tagged with MS-analyzable and releasable tags. The X-mers in the second X-mer mixture have both 5' and 3' hydroxyl termini (5'OH—OH3') and preferably but not necessarily are not tagged. This results in only 2X-mer ligation products having the form o—o/p—y and therefore only one orientation between the two ligation precursors after ligation. Blocking of the 3' terminus may be accomplished, for example, by employing a group that cannot undergo condensation, such as, for example, an unnatural group such as a 3'-phosphate, a 3'-terminal dideoxy, a polymer or surface, or other means for inhibiting ligation. This approach has great informational advantages because the two sets can be jointly optimized.

PEA and XLA possess a number of desirable attributes. First, all are solution-based systems and are governed by standard solution mass-action and diffusion processes. This stands in contrast to unassisted surface-based array hybridization systems, where the probe is physically attached to the surface and unable to diffuse, thus slowing the kinetics of hybridization. In contrast to surface-bound arrays, it is a characteristic of the present invention that a high multiplicity of oligonucleotides binds along the target sequence. This is likely to increase the overall efficiency of X-mer binding and the subsequent enzymatic reaction. Moreover, because the X-mer precursors are short, they are less likely to form intramolecular structures.

Second, PEA and XLA take advantage of highly specific enzymatic processes. In the case of PEA, the high degree of specificity of the polymerase for perfect duplexes essentially serves to "proof-read" the hybridization process by extending (and therefore marking for detection) only those primers that have hybridized to the correct target sequence. This "proof-reading" is likely to increase the overall specificity of the assay over that which can be obtained by unassisted hybridization methods. Both the efficiency and specificity of hybridization is likely to be increased by the ligase enzyme in XLA as well.

Third, unlike surface-base array hybridization systems that rely on the detection of the hybridization event itself, PEA and XLA can mark for detection even transiently stable primer-target interactions. The lifetime of the interaction between the X-mer precursors and the target only needs to be long enough to be recognized and acted upon by the polymerase or ligase. This allows a given target sequence to act as a template for multiple precursor binding and subsequent extension or ligation reactions. This cycling (and therefore amplification), and the ability to detect transient events, can increase the overall detection sensitivity of the methods over that which can be obtained using unassisted surface-based hybridization assays by increasing the number of X-mer sequence complementary and therefore that hybridize to target nucleic acids to greater than a 1:1 ratio. As discussed above, this type of reaction cycling could be externally facilitated by artificially cycling the temperature during the extension or ligation reaction.

The methods described herein are directed to interrogating targets free in solution. However, it is also contemplated that the XLA methodology can be used in conjunction with surface-bound oligonucleotides such as arrays of oligonucleotides to increase the overall resolving power of array systems. The arrays generally involve a surface containing a mosaic of different oligonucleotides that are individually localized to discrete, known areas of the surface. Such ordered arrays containing a large number of oligonucleotides have been developed as tools for high throughput analyses of genotype and gene expression. Oligonucleotides synthesized on a solid support recognize uniquely complementary nucleic acids by hybridization, and arrays can be designed to define specific target sequences, analyze gene expression patterns or identify specific allelic variations.

The present invention may be practiced using oligonucleotides attached to a support. Referring to FIG. 5, in the present invention arrays of oligonucleotides such as DNA arrays can be generated such that the DNA probes are attached to the surface at their 5' terminus through a linker. These surface bound probes also have 3' terminal hydroxyl groups.

Referring to FIG. 5, the Array-based X-mer Ligation Assay (AXLA) involves the following steps. In step 1, the target sample is hybridized to the surface-bound probes of the array under conditions that are compatible with the ligation reaction described above. The target nucleic acid can be either unlabeled or labeled with, for example, a fluorescent label and so forth. In step 2, the mixture of tagged X-mers is added to the array and allowed to randomly hybridize along the target according to Watson-Crick base-pairing rules. In step 3, those X-mers that hybridize adjacent to the surface bound oligonucleotides are ligated using a DNA ligase as described above. Since only the surface-bound oligonucleotides have 3'-terminal hydroxyl groups, ligation occurs only between those X-mers that are hybridized adjacent to a DNA probe, and not between X-mers that are hybridized adjacent to one another at other positions along the target. In step 4, the ligated X-mers are separated from the unligated X-mer precursors. In step 5, the tags from the separated and ligated X-mers are released through cleavage of cleavable linkers attaching the tags to the X-mers. In step 6, the set of released tags is analyzed by MS to provide sequence information on the target nucleic acid.

Additionally or alternatively, the released tags are analyzed by MS feature by feature (or set of features) along the array. In this way, the sequence information from the array-based probe is also determined to provide more sequence information on the target nucleic acid molecule and thus, greatly increasing the power of the array based XLA assay. The conditions for carrying out the ligation reactions in this approach are similar to those described above.

Design of Precursor X-mer Mixtures

The power of the assay(s) described above is dependent upon characteristics of the X-mer mixtures used to interrogate the target nucleic acid. As discussed above, a high degree of overlap of masses among X-mers having different sequence is an inescapable consequence of X-mers being composed of only four building blocks (see histogram of FIG. 1). The reagents of the present invention are designed to remove the problem stemming from the inherent molecular weight and sequence ambiguities resulting from the mass overlap from the MS analysis, thus, increase the power in all applications utilizing mass spectrometry to analyze the sequence of the target nucleic acid. This reduction is accomplished by employing a mixture ($\Omega$) of natural and/OR mass-modified X-mer precursors having a high sequence coverage complexity ($CC_M(\Omega)$) and MS tags covalently linked to the X-mer precursors through cleavable linkers. The mixtures of the invention are generic or universal in the sense that they may be utilized in any application whose goal is to determine sequence information of a target nucleic acid. Furthermore, the mixtures may be designed without reference to any a priori information about the target nucleic acid sequence, including the presence, location or identity of a mutation, for example. However, this is not meant to imply that the mixtures would not be useful in analyzing target nucleic acid sequences wherein some information was known a priori about the sequence or that prior information will not assist in interpretation of the mass spectra.

The set of tags in the mixture is chosen to reduce the performance demands of MS by having desired charge-to-mass ratios, and to reduce the ambiguity in MS sequence analysis of nucleic acids. Ideally, each sequence in the mixture is tagged with a unique molecular weight among the tags in the set. However, the present invention may also be practiced using a set of tags where each tag is assigned to multiple X-mer precursor sequences. Assignment of the tags to X-mer precursor sequences may be arbitrary. In other words, assignment of the tags to multiple X-mer precursors sequences may be performed without regard to sequences.

Assignment of the tags may also be performed by selecting X-mer precursors having different nucleotide compositions and sequences to be individually tagged to MS tags having identical molecular weights. One of ordinary skill in the art is capable of selecting X-mer precursors with differing nucleotide compositions and sequences for assignment to tags. However, based on theoretical calculations, assignment of particular X-mer precursor sequences to particular tags does not vastly improve the analysis of data obtained from nucleic acid analysis in accordance with the present invention (unpublished observations).

In one embodiment, the number of MS distinguishable tags in the mixture is at least 25%, 50%, 75%, or 100% of the mass number complexity (MNC) of a mixture having the same X-mer precursors but without the tags and linkers, where all the precursors are extended by one nucleotide (A, T, C, and G). For example, for a mixture of all tagged 6-mer precursors, the number of tags is compared to the PEA products of the 6-mers (i.e. all possible 7-mers). The MNC for a mixture comprising all possible 7-mers of natural nucleotides is approximately 53. Therefore, preferably the set of tags has a sequence resolving power at least as great as the mixture of natural X-mer PEA products. Preferably, the number of MS distinguishable tags in the mixture is at least 100% of the MNC of a mixture having the same X-mer precursors but without the tags and linkers, where all the precursors are extended by one nucleotide. Also the maximum number of MS distinguishable tags is the number of sequence distinguishable X-mer precursors in the mixture (i.e. for all 6-mers comprising natural nucleotides, the maximum number is 4,096).

In another embodiment, the number of MS distinguishable tags to be used in a mixture is determined as a percentage of the number of X-mer precursors in the mixture. Preferably, the number of MS distinguishable tags in a mixture is at least 0.5%, 1%, 2%, 5%, 10%, 20%, 25%, 50%, 75%, or 90% of the number of X-mer precursors in the mixture. As a non-limiting illustrative example, a mixture of all 4,096 6-mers comprising natural nucleotides when used in a PEA assay results in 7-mers. The MNC of a mixture of all 7-mers is approximately 53. Therefore, it is desirable that the number of MS distinguishable tags in a mixture of 6-mer oligonucleotide precursors in a PEA assay in accordance with the present invention is greater than about 50 (e.g. 50/4,096 is about 1%).

For specific applications (e.g. mutation detection; see Examples) the power of an assay can be measured in the length of target nucleic acid within which the problem can be solved (in this specific example, detection of a mutation) with a given success rate, say, 95%. As the power of the assay increases, the length that can be analyzed with a given success rate increases. The same holds true for the success rate with which given lengths can be analyzed. A good benchmark of usability is the length of DNA that can be analyzed on an automated DNA gel electrophoresis sequencer, typically 500 bases or so. A reasonable goal, then, is the analysis of 500 base targets with >95% success rate.

Analysis Step

After the step of processing of hybrids, the unprocessed X-mer precursors are separated from the processed X-mer precursors. Separation may be performed by a variety of methods known in the art such as MS, chromatography (e.g. HPLC; affinity chromatography; magnetic beads), or fluorescence activated sorting for methods that mark the processed oligonucleotides with a fluorescent marker. Examples of affinity methods would include employing biotinylated or digoxigenin labeled chain-termination nucleotides followed by purification of tagged X-mer extension products using streptavidin or antidigoxigenin pair (Kessler, *Advances in Mutagenisis*, Berlin/Heidelber; Springer-Verlag; 105-152 (1990)). Phenylboronic acid complexes may also be used for preparing other high affinity purification methods (U.S. Pat. No. 5,594,151).

After separation of the processed hybrids, the tags are released from the nucleic acid portion of the X-mer products by cleavage of the linkers. The tags are subsequently analyzed by means of mass spectrometry. The details of the analysis are known in the art and will not be repeated here. Suitable mass spectrometers are described in *Methods in Enzymology*, B. Karger & W. Hancock (editors), Academic Press, San Diego, V270 (1996) and *Methods in Enzymology*, J. McCloskey (editor), Academic Press, San Diego, V193 (1990). These include matrix assisted laser desorption/ionization ("MALDI"), electrospray ("ESI"), atmospheric pressure chemical ionization ("APCI"), ion cyclotron resonance ("ICR"), Fourier transform types and delayed ion extraction and combinations or variations of the above. Suitable mass analyzers include magnetic sector/magnetic deflection instruments in single quadrupole, triple ("MS/MS") quadrupole, Fourier transform and time-of-flight ("TOF") configurations and the like.

A preferred method is the use of MS-MS. It is known in the art that mass spectrometry can be used to separate molecular ions and then subject selected ions to fragmentation conditions in the mass spectrometer. This two-dimensional technique, known as MS-MS, is typically performed in a triple quad, ion trap or Q-TOF mass spectrometer.

In accordance with the present invention, triple quad MS-MS can be used to separate processed and unprocessed X-mer precursors in the first stage, to cleave the linkers to release the tags in the second stage, and to analyze the released tags in the third stage of a triple quad mass spectrometer to identify tags of processed X-mers to provide information on the sequence of the X-mers and therefore, the target nucleic acid.

Alternatively or additionally, as described above, the processed X-mers are separated from the unprocessed X-mers prior to MS analysis. Therefore, fragmentation to release the tags and subsequent MS analysis may be performed in a single stage using a single quadropole mass spectrometer, rather than a multi-stage mass spectrometer. Preferably, for single quadropole MS analysis, the molecular weight of the set of tags is distinguishable from the molecular weight of the processed X-mers after release of the tags. For details on MS methods, see Chernushevich and Thomson (EP1006559); Verentchikov et al. (WO/0077823); Clemmer and Reilly (WO/0070335); Hager (WO/0073750); WO9901889; the teachings of which are all incorporated herein by reference.

Data Analysis

After a mass spectrum is obtained, an analysis is performed to yield the information defined by the particular application. For example, mutation detection requires only a qualitative analysis of the data since these types of applications generally involve comparing the mass spectra between a reference sequence and an unknown variant thereof. If mass peak differences exists, then some type of mutation (or sequence difference) is present in the unknown variant.

Mutation identification requires more sophisticated analysis. As is the case in mutation detection, mutation identification generally involves a comparison between a reference sequence and an unknown variant. However, to identify the exact position and identity of a heterozygous mutation within the variant sequence, the following process is applied. First, identify peaks that appear in the sample mass spectrum that do not appear in the wild-type spectrum. Next, from the list of all possible product mixture X-mers, identify those that have masses consistent with the new peaks. Then, identify possible mutation sites that would lead to each of the product mixture X-mers identified being present. If the type of mutation is known (e.g. substitution), then many possible mutation sites may be rejected, and thus many X-mers may be rejected. Finally, test the theoretical spectrum of each mutation for consistency with the observed spectrum.

More sophisticated process can be employed to resolve ambiguities due to differences in extension or ligation efficiencies, ionization efficiencies and isotope effects. Moreover, depending upon the $CC_M$ and MNC of the set of tags in the mixture after release, de novo sequence information can also be obtained using algorithms similar to those developed for the sequencing using oligonucleotide arrays (see for example; Pevzner, P. A., *J. Biomolecular Structure Dynamics* 7, 63 (1989), Pevzner P.A., et al., *J. Biomolecular Structure Dynamics* 9, 399 (1991), Ukkonen, E., *Theoretical Computer Science* 92, 191 (1992)).

Kits of the Invention

Another aspect of the present invention relates to kits useful for conveniently performing a method in accordance with the invention. To enhance the versatility of the subject invention, the reagents can be provided in packaged combination, in the same or separate containers, so that the ratio of the reagents provides for substantial optimization of the method. The reagents may each be in separate containers or various reagents can be combined in one or more containers depending on the crossreactivity and stability of the reagents.

In one embodiment a kit comprises mixture or a set of sub-mixtures comprising nucleic acids and tags covalently attached to the nucleic acids through cleavable linkers for direct mass spectral analysis of the tags after release by cleavage of the linkers, where the tags are distinguishable by mass spectrometry and are assigned to known sequences of X-mer precursors. The mixture comprises X-mer precursors having a minimum length of 3 nucleotides. The minimum mixture coverage complexity ($CC_M$) of the mixture (or minimum composite mixture coverage complexity of the set of sub-mixtures) is 56 divided by N, where N is the number of distinct X-mers in the mixture. The length of the X-mer precursors can be selected independently for each X-mer precursor. Each of the X-mer precursors in the mixture is represented by a single chemical species. Each sub-mixture in the set has a reduced mixture coverage complexity relative to the composite mixture coverage complexity. Further, each sub-mixture comprises a plurality of X-mer precursors.

In another embodiment a kit comprises a mixture as described above, an enzyme having a nucleotide polymerase activity, and a multiplicity of nucleotides selected from the group consisting of natural chain-terminating triphosphates.

In another embodiment a kit comprises a mixture as described above, an enzyme having a nucleotide polymerase activity, a multiplicity of nucleotides selected from the group consisting of natural chain-terminating triphosphates and extension nucleotide triphosphates.

In another embodiment a kit comprises a mixture as described above, an enzyme having a nucleotide polymerase activity, a multiplicity of nucleotides selected from the group consisting of mass-modified chain-terminating triphosphates and extension nucleotide triphosphates.

In another embodiment a kit comprises a mixture as described above and a DNA ligase.

In another embodiment a kit comprises a mixture as described above and a condensing agent.

In another embodiment, a kit comprises a mixture as described above and reagents for purification of reaction products as described herein.

Another embodiment of the present invention is a kit for carrying out a method as described above. The kit comprises a mixture as described above, a DNA ligase and an array comprising a surface and a multiplicity of nucleic acid sequence probes attached to the surface and a nucleic acid sequence having a terminal 3'-hydroxyl end.

In one aspect a kit comprises a condensing agent, an array comprising a surface and a multiplicity of nucleic acid sequence probes having a terminal 3'-hydroxyl end.

The kit can further include other separately packaged reagents for conducting the method as well as ancillary reagents and so forth. The relative amounts of the various reagents in the kits can be varied widely to provide for concentrations of the reagents that substantially optimize the reactions that need to occur during the present method. Under appropriate circumstances one or more of the reagents in the kit can be provided as a dry powder, usually lyophilized, including excipients, which on dissolution will provide for a reagent solution having the appropriate concentrations for performing a method in accordance with the present invention. The kit can further include a written description of a method in accordance with the present invention as described above.

The reagents, methods and kits of the invention are useful for, among others, mutation detection, mutation identification, polymorphism analysis, genotyping, de novo sequencing, re-sequencing, gene expression profiling, cDNA clustering and the like.

It should be understood that the above description is intended to illustrate and not limit the scope of the invention. Other aspects, advantages and modifications within the scope of the invention will be apparent to those skilled in the art to which the invention pertains. The following examples are put forth so as to provide those of ordinary skill in the art with examples of how to make and use the method and products of the invention, and are not intended to limit the scope of what the inventors regard as their invention.

EXAMPLES

The following examples relate to the methods described above using a region of the human p53 gene sequence as the target nucleic acid. FIG. 7 shows a 62 nucleotide region of the p53 gene with a known mutation site indicated in bold face. For all analyses, the complement of the sequences given in FIG. 7 is used. All of the examples are simulations. Therefore, the specifics with regard to the reaction conditions (i.e. buffer, X-mer and target concentrations, polymerase or ligase type etc.) are not relevant here. Interpretation of these examples depends only upon the mass complexity and coverage complexity of the X-mer precursors, the target length and sequence and the type of assay employed. All examples assume that the reactions proceed as they are described throughout the text and indicated in the figures. Importantly, it is assumed that only those X-mers that are exact complements of the target sequence are actually extended (in the cases of PEA) or ligated (in the case of XLA). The main purpose of all of the examples is to illustrate the theoretical power of each assay in terms of the type of mass spectra and information content that each assay would generate.

Example 1

Understanding the Power of CMT-PEA as a function of X-mer Composition and Tag Number The informational aspects and the effect of various design parameters of the present invention were realized by studying the application of PEA using cleavable mass tagged (CMT) X-mer precursors for heterozygous mutation detection. In this analysis, one randomly draws a sequence of length L and randomly changes (mutates) the middle base. The question is asked whether the sequence variants have a peak in their theoretical assay spectrum that does not appear in the other's (mutants) spectrum. A positive answer means that if this were a true, a mutation could be detected in a normal population assuming a threshold allele frequency and either an integrated or binary (yes or no) reading of the CMT mass spectra.

Figure 6:
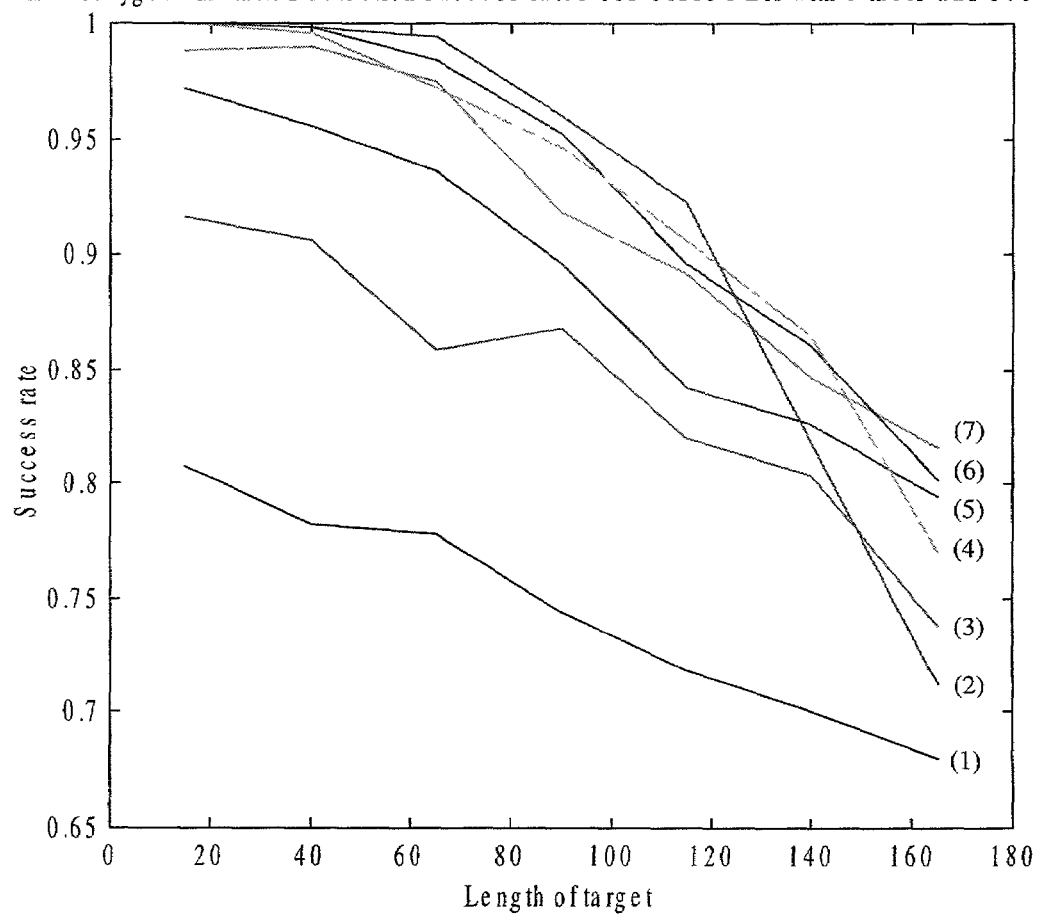
FIG. 6 is a diagram showing the relationship between heterozygous mutation detection success rate and target length for 1000 (1), 1500 (2), 2000 (3), 2500 (4), 3000 (5), 3500 (6) and 4000 (7) of the 4,096 6-mers tagged arbitrarily with 100 CMTs having different masses.

FIG. 6 depicts mutation detection success rates using 6-mers and 100 CMTs.

The different curves represent different set sizes of the total possible number of 4,096 6-mers actually tagged. Therefore the different curves represent different sequence coverage values for the 6-mer mixture. Set sizes covered are 1000 through 4000, in steps of 500 where each member of the set was chosen randomly. The assignment of the mass tags to the 6-mer sequences is arbitrary. As evident in the graph, a higher success rate is obtained when a greater number of total possible 4,096 6-mer sequences are utilized with an optimum approaching approximately 3000 6-mers. That only a subset of the total possible 4,096 6-mer are necessary to having sufficient sequence coverage is consistent with that taught in U.S. Ser. No. 09/112,437. Using approximately 3000 6-mers, mutation detection can be achieved at a success rate of ~95% using targets of length of about 100 nucleotides. As the number of cleavable tags (CMTs) is increased, the ambiguity is reduced which effectively increases the target length that can be interrogated at a given success rate (data not show).

Example 2

Theoretical Analysis of a p53 Gene Target Fragment using CMT-PEA

The following example relates to the CMT-PEA method described above using a region of the human p53 gene sequence as the target nucleic acid sequence. FIG. 7 shows a 62 nucleotide region of the p53 gene with known mutation sites indicated in bold face.

All of the examples are simulations. Therefore, the specifics with regard to the reaction conditions (i.e. buffer, X-mer and target concentrations, polymerase or ligase type, temperature, etc.) are not relevant here. Interpretation of these examples depends only upon the number of CMTs employed, coverage complexity of the X-mer precursors, the target length and sequence and the type of assay employed. All examples assume that the reactions proceed as they are described throughout the text and indicated in the figures. Importantly, it is assumed that only those X-mers that are exact complements of the target sequence are actually extended. The main purpose of all of the examples is to illustrate the theoretical power of each assay in terms of the type of mass spectra and information content that each assay would generate.

PEA is performed using the 62 nucleotide p53 fragment as the target and a sequence-complete set (all 4,096) of 6-mers having 100 CMTs with a mass range of 101 to 200 arbitrarily assigned to the mixture. FIG. 7 gives the set of 56 overlapping 7-mer extension products that are expected for the wild type p53 target sequence. The CMT mass spectra of the 7-mer PEA products corresponding to the wild type (Target G) and the single G2481C (Target C) and G2481T (Target T) mutants are given in FIG. 8. The integrated difference spectra in FIG. 9A & 9B reveal which CMT masses differ between the wild type and the two mutants. Positive difference peaks correspond to masses present in the wild type but not in the mutant whereas negative difference peaks correspond to masses in the mutant but not the wild type. In this example, one observes the theoretical maximum number of differences (6 positive and 6 negative) for the G2481C. mutant and less than the theoretical maximum number of differences (5 positive and 5 negative (two are very close together)) for the G2481T mutant.

It is important to emphasize however, that the information revealed in the integrated difference spectra assumes that the hybridization, extension, separation, ionization, and detection steps for all X-mers and corresponding CMTs occur with equal efficiencies. Because this level of quantitation is unlikely to be the case, even with good optimization, the individual spectral data is reduced to a binary form (FIGS. 9C & D). This type of transformation then requires only that the above steps meet a defined threshold level. Although this elimination of the quantitative nature of the data can reduce the overall power the assay, the resulting binary difference spectra still reveals differences between the wild type and mutant; 3 positive and 3 negative for the G2481C mutant and 3 positive and 2 negative for the G2481T mutant.

The 62 nucleotide p53 target fragment and related mutants were then interrogated with a sequence-complete set (all 4,096) of 6-mers having 400 CMTs with a mass range of 101 to 500 arbitrarily assigned to the mixture (FIG. 10). A comparison of the integrated and binary difference spectra for the G2481C and G2481T mutants reveal that there is no loss of information in the binary mode (FIG. 11). This is due to a decrease in the ambiguity of the CMT 6-mer mixture and resulting decreased likelihood of mass overlap for the individual CMT components (corresponding 6-mers) that reflect a given target sequence.

Figure 12:
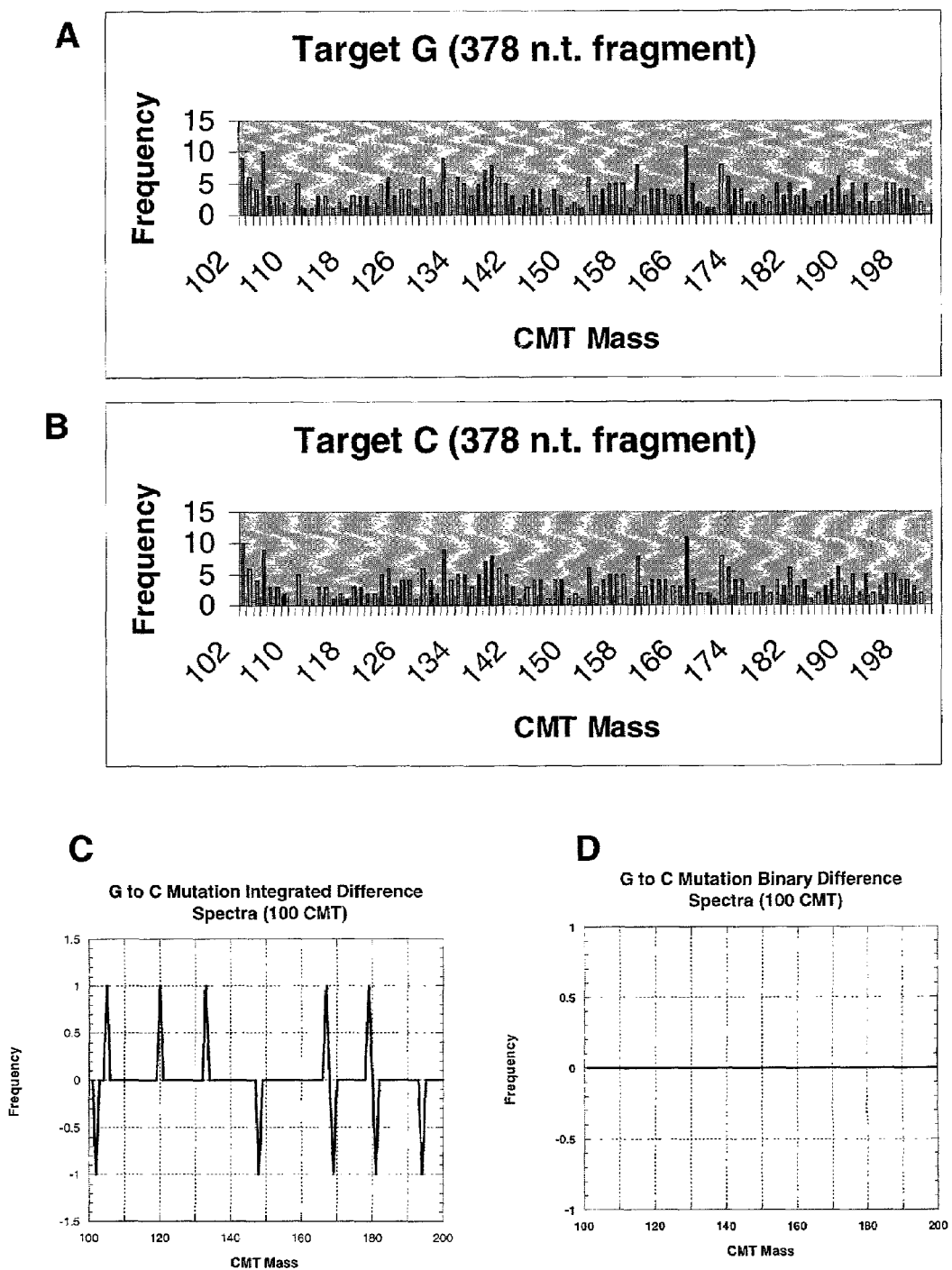
FIG. 12 depicts mass spectra of CMT-PEA analysis for (A) the wild type; (B) G to C; p53 mutant within a 378 nucleotide target fragment using 100 CMTs arbitrarily assigned to 4,096 6-mers. (C) depicts the integrated spectrum; (D) depicts the binary transformed difference spectrum for the G to C mutation.
Figure 13:
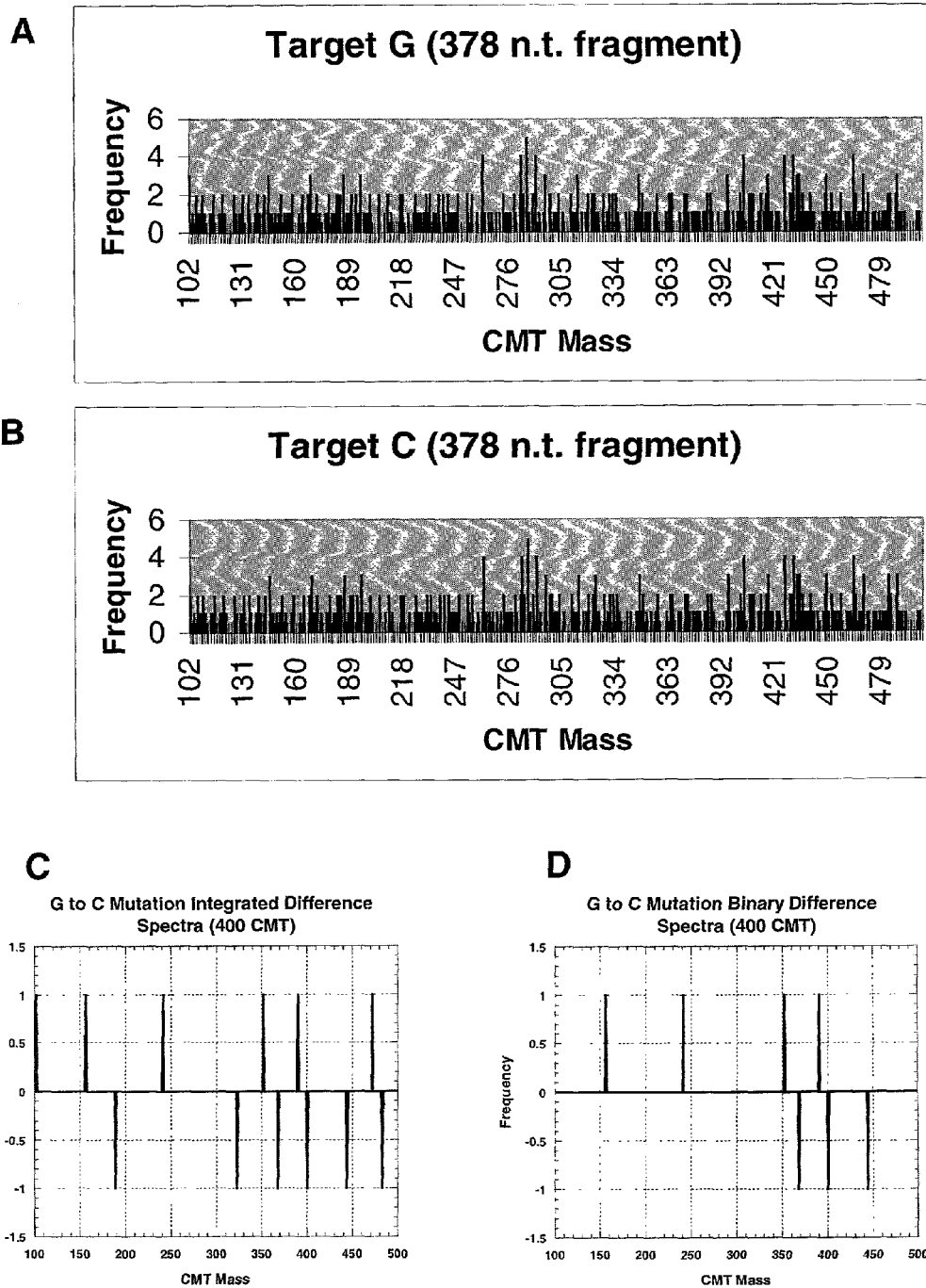
FIG. 13 depicts mass spectra of CMT-PEA analysis for (A) the wild type; (B) G to C; p53 mutant within a 378 nucleotide target fragment using 400 CMTs arbitrarily assigned to 4,096 6-mers. (C) depicts the integrated spectrum; (D) depicts the binary transformed difference spectrum for the G to C mutation.

To show the effect of increasing the number of CMTs on the power of assay, and thereby reducing the ambiguity of CMT mass signature and allowing the interrogation of longer target fragments, the CMT-PEA assay was modeled where the wild type p53 sequence and G2481C mutant were embedded in a 378 nucleotide long target fragment. FIG. 12 shows the theoretical CMT spectra for the (A) wild type and (B) G2481C mutant using 100 CMTs. The integrated difference spectra (FIG. 12C) reveals all 12 possible differences between the wild type and the G2481C mutant. The binary difference spectra, however, reveals no differences between the two sequences. If however the CMT-PEA assay is performed using a 6-mer mixture (all 4,096) having 400 CMTs, the binary difference spectra reveals 7 of the 12 possible differences (FIG. 13A-C). Again, this is due to a decrease in the ambiguity of the CMT 6-mer mixture which decreases the likelihood of mass overlap for the individual CMT components that reflect a given target sequence.

All publications and patent applications cited in this specification are herein incorporated by reference as if each individual publication or patent application where specifically and individually indicated were incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:

1. A mixture or set of sub-mixtures comprising X-mer precursors of different length,
   wherein the X-mer precursors have a minimum length of 3 nucleotides;
   wherein the mixture has a minimum mixture coverage complexity of at least 56/N or wherein the set of sub-mixtures has a composite mixture coverage complexity of at least 56/N, wherein N represents the number of distinct X-mer precursors in the mixture;
   wherein each sub-mixture in said set has a reduced mixture coverage complexity as compared with the composite mixture coverage complexity;
   wherein each sub-mixture comprises a plurality of X-mer precursors;
   wherein said length is selected independently for each X-mer precursor; and
   wherein the mixture or set of sub-mixtures further comprises a set of tags that are distinguishable by mass spectrometry, wherein each tag is covalently linked to at least one X-mer precursor through a cleavable linker such that any given oligonucleotide sequence in the mixture is attached to a single tag with a discrete molecular weight.

2. A mixture or set of sub-mixtures comprising X-mer precursors of different length,
   wherein said X-mer precursors have a minimum length of 3 nucleotides;
   wherein said mixture has a minimum mixture coverage complexity of at least 56/N or wherein said set of sub-mixtures has a composite mixture coverage complexity of at least 56/N, wherein N represents the number of distinct X-mer precursors in the mixture;
   wherein each sub-mixture in said set has a reduced mixture coverage complexity as compared with the composite mixture coverage complexity;
   wherein each sub-mixture further comprises a plurality of X-mer precursors;
   wherein said length is selected independently for each X-mer precursor;
   wherein the mixture or set of sub-mixtures further comprises a set of tags, wherein each tag is covalently linked to at least one X-mer precursor through a cleavable linker such that any given oligonucleotide sequence in the mixture is attached to a single tag with a discrete molecular weight; and
   wherein said X-mer precursors have a determined isotopic composition.

3. The mixture or set of sub-mixtures of claim 1 or 2 wherein said mixture has a mixture coverage complexity of at least about 1/2 when said mixture contains at least 128 discrete X-mers, or wherein said set of sub-mixtures has a composite mixture coverage complexity of at least about 1/2 when said set of sub-mixtures contains at least 128 discrete X-mers.

4. The mixture or set of sub-mixtures of claim 1 or 2, wherein said mixture has a mixture coverage complexity of at least about 1/4 when said mixture contains at least 256 discrete X-mers, or wherein said set of sub-mixtures has a composite mixture coverage complexity of at least about 1/4 when said set of sub-mixtures contains at least 256 discrete X-mers.

5. The mixture or set of sub-mixtures of claim 1 or 2, wherein said mixture has a mixture coverage complexity of at least about 1/8 when said mixture contains at least 512 discrete X-mers, or wherein said set of sub-mixtures has a composite mixture coverage complexity of at least about 1/8 when said set of sub-mixtures contains at least 512 discrete X-mers.

6. The mixture or set of sub-mixtures of claim 1 or 2, wherein nucleotide sequences of the precursors of said mixture or set of sub-mixtures are known.

* * * * *